US012765910B2

(12) United States Patent
Norton et al.

(10) Patent No.: US 12,765,910 B2
(45) Date of Patent: Oct. 20, 2026

(54) ARTHROSCOPIC DEVICES AND METHODS

(71) Applicant: Relign Corporation, Santa Clara, CA (US)

(72) Inventors: Jeff Norton, Emerald Hills, CA (US); Simon Malkevich, Gilroy, CA (US); Aaron Germain, San Jose, CA (US)

(73) Assignee: Relign Corporation, Santa Clara, CA (US)

( * ) Notice: Subject to any disclaimer, the term of this patent is extended or adjusted under 35 U.S.C. 154(b) by 383 days.

(21) Appl. No.: 18/278,953

(22) PCT Filed: Feb. 18, 2022

(86) PCT No.: PCT/US2022/017045
§ 371 (c)(1),
(2) Date: Aug. 25, 2023

(87) PCT Pub. No.: WO2022/191978
PCT Pub. Date: Sep. 15, 2022

(65) Prior Publication Data

US 2024/0293140 A1 Sep. 5, 2024

Related U.S. Application Data

(60) Provisional application No. 63/159,819, filed on Mar. 11, 2021.

(51) Int. Cl.
*A61B 17/00* (2006.01)
*A61B 17/32* (2006.01)

(52) U.S. Cl.
CPC *A61B 17/32002* (2013.01); *A61B 2017/0088* (2013.01); *A61B 2017/320024* (2013.01); *A61B 2217/005* (2013.01); *A61B 2217/007* (2013.01)

(58) Field of Classification Search
CPC .............. A61B 2017/320032; A61B 17/32002
See application file for complete search history.

(56) References Cited

U.S. PATENT DOCUMENTS 6,610,059 B1 * 8/2003 West, Jr. .............. A61B 18/148 606/41
8,029,524 B1 * 10/2011 Mitusina .......... A61B 17/32002 606/167

(Continued)

FOREIGN PATENT DOCUMENTS

WO WO-2022191978 A1 9/2022

OTHER PUBLICATIONS

"International Application Serial No. PCT US2022 017045, International Preliminary Report on Patentability mailed Sep. 21, 2023", 7 pgs.

(Continued)

*Primary Examiner* — Nicholas W Woodall
(74) *Attorney, Agent, or Firm* — SCHWEGMAN LUNDBERG & WOESSNER, P.A.

(57) ABSTRACT

A radiofrequency (RF) device for treating tissue in the presence of an electrically conductive fluid includes an outer tube, an inner tube, a wire tube, an electrode, and a wire. The outer tube forms a bend located proximate a distal end. Each of the inner tube and the wire tube extends from the proximal end of the outer tube to the distal end of the outer tube. Tire inner tube and the wire tube each define segmented portions located at the bend of the outer tube. The electrode is connected to the inner tube at a distal end of the inner tube. The segmented portions are each configured to allow the inner tube, the wire tube, and the wire, to respectively flex proximate the bend upon rotation of the inner tube, the warm tube, and the wire about the axis of the outer tube.

20 Claims, 21 Drawing Sheets

(56) References Cited

U.S. PATENT DOCUMENTS

| | | | | |
|---|---|---|---|---|
| 8,486,096 | B2 * | 7/2013 | Robertson | A61N 7/022 606/169 |
| 9,855,675 | B1 | 1/2018 | Germain et al. | |
| 10,022,140 | B2 | 7/2018 | Germain et al. | |
| 10,052,149 | B2 | 8/2018 | Germain et al. | |
| 10,525,231 | B2 * | 1/2020 | Moquin | A61L 29/06 |
| 10,595,889 | B2 | 3/2020 | Germain et al. | |
| 2002/0038129 | A1 * | 3/2002 | Peters | A61B 17/32002 606/167 |
| 2011/0022069 | A1 * | 1/2011 | Mitusina | A61B 17/32002 606/180 |
| 2012/0109130 | A1 * | 5/2012 | Casey | A61B 17/32002 606/79 |
| 2013/0041392 | A1 * | 2/2013 | Edwards | A61B 17/3207 606/1 |
| 2015/0202001 | A1 | 7/2015 | Mitchell et al. | |
| 2016/0022301 | A1 | 1/2016 | Obrien | |
| 2016/0346036 | A1 * | 12/2016 | Orczy-Timko | A61B 18/1206 |
| 2016/0346037 | A1 | 12/2016 | Truckai et al. | |
| 2017/0119363 | A1 * | 5/2017 | Nguyen | A61B 17/00234 |
| 2017/0202612 | A1 | 7/2017 | Germain et al. | |
| 2017/0224368 | A1 | 8/2017 | Germain et al. | |
| 2017/0258519 | A1 | 9/2017 | Germain et al. | |
| 2017/0290602 | A1 | 10/2017 | Germain et al. | |
| 2018/0263649 | A1 | 9/2018 | Germain et al. | |
| 2018/0303509 | A1 | 10/2018 | Germain et al. | |
| 2018/0317957 | A1 | 11/2018 | Germain et al. | |
| 2019/0008538 | A1 | 1/2019 | Germain et al. | |
| 2019/0008541 | A1 | 1/2019 | Norton et al. | |
| 2019/0015151 | A1 | 1/2019 | Germain et al. | |
| 2019/0021788 | A1 | 1/2019 | Germain et al. | |
| 2019/0059983 | A1 | 2/2019 | Germain et al. | |
| 2019/0083121 | A1 | 3/2019 | Benamou et al. | |
| 2019/0134279 | A1 | 5/2019 | Benamou et al. | |
| 2022/0218380 | A1 * | 7/2022 | Magno | A61B 17/320016 |

OTHER PUBLICATIONS

"European Application Serial No. 22710222.5, Response Filed Apr. 16, 2024 to Communication pursuant to Rules 161(1) and 162 EPC mailed Dec. 20, 2023", 19 pgs.
"International Application Serial No. PCT/US2022/017045, International Search Report mailed Jun. 7, 2022", 4 pgs.
"International Application Serial No. PCT/US2022/017045, Written Opinion mailed Jun. 7, 2022", 5 pgs.

* cited by examiner

ARTHROSCOPIC DEVICES AND METHODS

PRIORITY CLAIM

The present application is a U.S. National Stage Application under 35 U.S.C. 371 from International Application Serial No. PCT/US2022/017045, filed on Feb. 18, 2022, and published as WO 2022/191978 A1 on Sep. 15, 2022, which claims priority to U.S. Provisional Application No. 63/159,819, entitled "Arthroscopic devices and Methods," filed on Mar. 11, 2021; the contents of each of which are hereby incorporated by reference in their entirety.

FIELD OF THE INVENTION

The present invention relates generally to apparatus and methods for endoscopic and other surgical procedures and, more particularly, to apparatus and methods for cutting and removal of bone and soft tissue.

BACKGROUND

A variety of apparatus and methods exist for endoscopic cutting and removal of bone including for example subacromial decompression, anterior cruciate ligament reconstruction involving notchplasty, and arthroscopic resection of the acromioclavicular joint. Currently, surgeons use arthroscopic shavers and burrs having rotational cutting surfaces to remove hard tissue in such procedures.

To promote efficiency, endoscopic tool systems including a reusable handpiece and a selection of interchangeable tool probes having different working ends are available. Individual working ends may each have two or more functionalities, such as soft tissue removal and hard tissue resection, so such tools systems can provide dozens of specific functionalities, providing great flexibility.

While a significant advantage, the need for one tool system to accommodate such flexibility is a challenge. In particular, many of the probes for these systems include lumens within rotatable shafts for the vacuum aspiration of fluids and tissue debris from the working site. As many of these rotatable tools also rely on the delivery of radiofrequency (RF) current from the handpiece to the working end of the probe, the interface between the reusable handpiece and the replaceable (usually disposable) probe must be designed to allow mechanical and electrical connection while managing fluid exchange so that the tools may be operated without electrical shorting.

It is therefore an object of the present invention to provide improved surgical systems and methods for their use, such as improved arthroscopic and other endoscopic tissue cutting and removal system wherein a reusable or other handpiece may be removably connected to the replaceable, usually disposable, probe while permitting vacuum aspiration of fluids and tissue debris through a probe shaft and outwardly through the handpiece without interfering with the electrical and/or mechanical operation of the surgical system. At least some of these objectives will be met by the inventions described herein.

2. Description of the Background Art. Relevant commonly owned patent publications include: US 2018-0303509; US 2019-0008541; US 2019-0059983; US 2019-0134279; US 2019-0021788; US 2018-0317957; US 2019-0008538; US 2019-0083121; US 2018-0263649; and US 2019-0015151, the full disclosures of which are incorporated herein by reference.

SUMMARY OF THE INVENTION

The following, non-limiting examples, detail certain aspects of the present subject matter to solve the challenges and provide the benefits discussed herein, among others.

Example 1 is a device for treating tissue, device comprising: an outer tube having an axis that extends from a proximal end and a distal end, the outer tube forming a bend located proximate the distal end; an inner tube located at least partially inside the outer tube and extending from the proximal end of the outer tube to the distal end of the outer tube, the inner tube defining a first segmented portion located at the bend of the outer tube; a wire tube located at least partially inside the inner tube and extending from the proximal end of the outer tube to the distal end of the outer tube, the wire tube defining a second segmented portion located at the bend of the outer tube and the first segmented portion; an electrode connected to the inner tube at a distal end of the inner tube; and a wire located at least partially inside the wire tube and connected to the electrode, the wire extending from the electrode to the proximal end of the outer tube, wherein the first segmented portion and the second segmented portion are each configured to allow the inner tube, the wire tube, and the wire, to respectively flex proximate the bend upon rotation of the inner tube, the wire tube, and the wire about the axis of the outer tube.

In Example 2, the subject matter of Example 1 optionally includes wherein the first segmented portion includes a plurality of interlocking finger.

In Example 3, the subject matter of any one or more of Examples 1-2 optionally include wherein the second segmented portion is defined by a spiral patterned cut formed in the wire tube.

In Example 4, the subject matter of any one or more of Examples 1-3 optionally include wherein the wire tube is connected to the inner tube proximate a distal and proximal end of the first segmented portion.

In Example 5, the subject matter of any one or more of Examples 1-4 optionally include wherein the inner tube defines: a first opening proximate the distal end of the outer tube and a first fluid pathway extending from the first opening to the proximal end of the outer tube during an ablation operation, and a second opening located in between the first opening and the proximal end of the outer tube and a second fluid pathway extending from the second opening to the proximal end of the outer tube during a burring operation.

In Example 6, the subject matter of any one or more of Examples 1-5 optionally include wherein the electrode is recessed into a ceramic insulator attached to a distal end of the inner tube.

In Example 7, the subject matter of any one or more of Examples 1-6 optionally include a burr tool located proximate the electrode.

In Example 8, the subject matter of any one or more of Examples 1-7 optionally include a shaver tool located proximate the electrode.

In Example 9, the subject matter of any one or more of Examples 1-8 optionally include a hub attached to the proximal end of the outer tube, the hub detachably connectable to a handpiece.

In Example 10, the subject matter of Example 9 optionally includes wherein the hub comprises an active radiofrequency contact in electrical communication with the wire.

Example 11 is a device for treating tissue, device comprising: an outer tube having an axis that extends from a proximal end and a distal end, the outer tube forming a bend located proximate the distal end; an inner tube located at least partially inside the outer tube and extending from the proximal end of the outer tube to the distal end of the outer tube, the inner tube defining a first segmented portion located at the bend of the outer tube; a wire tube located at least partially inside the inner tube and extending from the proximal end of the outer tube to the distal end of the outer tube, the wire tube defining a second segmented portion located at the bend of the outer tube and the first segmented portion; a tip assembly located at a distal end of the inner tube, the tip assembly defining a recess and cutting surface; an electrode located within the recess; and a wire located at least partially inside the wire tube and connected to the electrode, the wire extending from the electrode to the proximal end of the outer tube, wherein the first segmented portion and the second segmented portion are each configured to allow the inner tube, the wire tube, and the wire, to respectively flex proximate the bend upon rotation of the inner tube, the wire tube, and the wire about the axis of the outer tube.

In Example 12, the subject matter of Example 11 optionally includes wherein the first segmented portion includes a plurality of interlocking finger.

In Example 13, the subject matter of any one or more of Examples 11-12 optionally include wherein the second segmented portion is defined by a spiral patterned cut formed in the wire tube.

In Example 14, the subject matter of any one or more of Examples 11-13 optionally include wherein the wire tube is connected to the inner tube proximate a distal and proximal end of the first segmented portion.

In Example 15, the subject matter of any one or more of Examples 11-14 optionally include a ceramic insulator located in the recess, the electrode located within a recess defined by the ceramic insulator.

In Example 16, the subject matter of any one or more of Examples 1-15 optionally include wherein the tip assembly includes a burr tool located proximate the electrode.

In Example 17, the subject matter of any one or more of Examples 11-16 optionally include wherein the tip assembly includes a shaver tool located proximate the electrode.

In Example 18, the subject matter of any one or more of Examples 11-17 optionally include wherein the inner tube defines: a first opening proximate the distal end of the outer tube and a first fluid pathway extending from the first opening to the proximal end of the outer tube during an ablation operation, and a second opening located in between the first opening and the proximal end of the outer tube and a second fluid pathway extending from the second opening to the proximal end of the outer tube during a burring operation.

In Example 19, the subject matter of any one or more of Examples 11-18 optionally include a hub attached to the proximal end of the outer tube, the hub detachably connectable to a handpiece.

In Example 20, the subject matter of Example 19 optionally includes wherein the hub comprises an active radiofrequency contact in electrical communication with the wire.

In Example 21, the devices or systems of any one or any combination of Examples 1-20 can optionally be configured such that all elements or options recited are available to use or select from.

The present invention provides improved surgical systems and methods for their use. In particular, the present invention provides improved arthroscopic or other endoscopic tissue cutting and removal methods and tools. The tools comprise, for example, a reusable or other handpiece which is removably connectible to a replaceable, usually disposable, probe. An interface between a proximal end of the probe and a distal and of the handpiece will be configured to permit vacuum aspiration of fluids and tissue debris through the probe shaft and outwardly through the handpiece while simultaneously providing an electrical interconnection to deliver radiofrequency (RF) current and/or mechanical driving force from the handpiece to the probe without interference from or with the vacuum aspiration.

In a first aspect, the present invention provides a bipolar RF device for treating tissue in the presence of an electrically conductive fluid. The bipolar RF device comprises a handpiece and a probe. The handpiece will typically include a motor drive, a receiving channel, and an active electrical contact on an inner wall of the receiving channel. A return electrical contact is usually also formed on the inner wall of the receiving channel and will be disposed proximally of the active electrical contact. The probe includes a proximal hub and an elongated shaft extending distally along an axis which extends longitudinally from the proximal hub. The hub is typically configured for detachable insertion into the receiving channel of the handpiece. A working end is located at a distal end of the elongated shaft and typically has an active electrode and a return electrode. A return electrical contact and an active electrical contact are each disposed on an outer surface of the proximal hub on the probe. In particular, the return electrical contact will be disposed proximally of the electrical contact so that (1) the return electrical contacts in the receiving channel and on the outer surface of the hub, respectively, and (2) the active electrical contacts in the receiving channel and on the outer surface of the hub, respectively, engage each other when the hub is inserted into the receiving channel of the handpiece.

By disposing the return electrical contacts on both the hub and in the receiving channel of the probe proximally of the active electrical contacts, it is easier to isolate the active contacts from fluids being aspirated through an aspiration lumen of the probe. In particular, as the return electrodes and return electrical contacts will typically be maintained at the electrical potential of the electrically conductive fluid in the surgical worksite (the fluid can act as a parallel ground path) so that electrical contact between the return electrical contacts and the fluid will be advantageous. Conversely, electrical isolation of the active electrical contacts is necessary to avoid electrical shorting.

In specific embodiments of the bipolar RF device, the probe may comprise or have a flow channel extending through the shaft to an exit port in the hub. The hub may comprise an interior chamber and outflow passageway, where an outlet end of the flow channel in the shaft opens to the interior chamber through the inner wall of the receiving channel. In further examples, the flow channel may extend from a window in the working end of the probe to the exit port in the hub and may be configured to remove fluids and tissue debris from a treatment site. In still further instances, the interior chamber and the outflow passageway in the hub may be configured for coupling to a negative pressure source in order to initiate vacuum aspiration through the window in the working end, the fluid passageway, the interior chamber, and the outflow passageway.

In other embodiments, a seal may be disposed between the outer surface of the hub and the inner wall of the receiving channel to inhibit fluid migration between the active electrical contacts and the return electrical contacts when the hub is inserted into the receiving channel of the handpiece. Such a seal allows exposure of the return electrical contacts to the aspiration fluid while isolating the active electrical contacts from said fluid. The seal may comprise, for example, a resilient member carried by the hub, the handpiece, or both. In particular instances, the dimensions of the outer surface of the hub and the inner wall of the receiving channel will be selected to provide a gap between the outer surface and the inner wall. The gap will be chosen typically to be sufficiently large to permit fluid migration from the chamber through the gap when the hub is inserted into the receiving channel of the hand piece. In such instances, the seal will be present to isolate the active electrical contacts from the aspiration fluids while allowing such fluids to contact the return electrical contacts.

In yet another specific embodiment, the active and return electrical contacts on the hub may each comprise a pair of diametrically opposed, spring-loaded electrodes or other contacts, and the active and return electrode contacts on the inner wall of the receiving channel may each comprise a ring electrode which extends 360° over a full circumference of the inner wall of the receiving channel. In specific examples, the pair of diametrically opposed, spring-loaded return electrical contacts will be electrically coupled to an outer sleeve of the probe (which acts as a ground in the bipolar treatment system) which in turn is coupled by a cylindrical core member which extends distally of the active electrical contacts. In still further instances, the pair of diametrically opposed, spring-loaded active electrodes contacts may pass radially through the cylindrical, typically through apertures or passageways through a wall of the core, and may be electrically coupled to an inner sleeve of the shaft by a rotating collar which is co-axially disposed within the cylindrical core member.

In a second aspect, a bipolar RF device for treating tissue in a patient in the presence of an electrically conductive fluid comprises a handpiece and a probe. The handpiece includes an interior chamber and outflow passageway and is adapted for gripping by the hand of an operator, i.e. for manual manipulation and operation. The probe comprises a proximal hub and an elongated shaft which extends distally about a longitudinal axis from the proximal hub. The probe has a working end at its distal end, and the working end includes active and return electrodes. The hub is configured for detachable insertion into a receiving channel of the handpiece. The first and second return electrical contacts are disposed in the receiving channel and on the hub, respectively, and are adapted to engage one another to connect the return electrode to an RF source when the hub is inserted into the receiving channel of the hand piece. A flow channel extends through the probe shaft in the hub and communicates with the interior chamber and the outflow passageway in the handpiece when the hub is inserted into the receiving channel of the handpiece. A gap will be maintained between the outer surface of the hub and the inner wall of the receiving channel, where the gap will typically be sufficiently large to permit fluid migration from the chamber through the gap when the hub is inserted into the receiving channel of the handpiece and the working end is immersed in such a fluid. A seal is disposed between the outer surface of the hub and the inner wall of the receiving channel to inhibit fluid migration between the active electrical contacts and the return electrical contacts so that the return electrical contacts may be exposed to fluid migrating inwardly through the gap while the active electrical contacts remain isolated from such fluid migration.

In specific instances, a selected portion of the flow channel comprises a dielectric to thereby control a distance between the active electrode and the first and second return electrical contacts. The distance may be controlled to permit a limited RF current flow from conductive fluid in the interior chamber to said first and second return electrical contacts while maintaining sufficient RF current flow between the active and return electrodes in the working end to ignite a plasma about the active electrode.

In other instances, the bipolar RF device may further comprise first and second return electrical contacts in the receiving channel and the hub, respectively, where the contacts are adapted to engage each other when the hub is inserted into the receiving channel of the handpiece.

In a third aspect, the present invention provides a bipolar RF device for treating tissue in the presence of an electrically conductive fluid. The device comprises an elongated probe having an outer sleeve assembly and an inner sleeve assembly. The inner sleeve assembly extends coaxially along a longitudinal axis of the probe to a working end which carries first and second electrodes, where an outer surface of the inner sleeve and an inner surface of the outer sleeve are separated by a gap. The outer and inner sleeve assemblies comprise first and second conductors which connect to the first and second electrodes, respectively. Dimensions of the outer surface of the inner sleeve and the inner surface of the outer sleeve are selected to provide a gap which has a target electrical resistance when a conductive fluid is disposed in the gap.

In specific instances, the bipolar RF device further comprises a handpiece with a motor drive and a proximal hub, where a portion of the probe is configured to be detachably received in a receiving channel in the handpiece. The bipolar RF device may still further comprise first and second electrical contacts in the handpiece and hub, respectively, w % here the electrical contacts are adapted to engage one another when the proximal portion of the hub is inserted into the receiving channel of the handpiece. Often, a flow channel is provided to extend through the elongated probe and to communicate with an interior chamber and an outflow passageway in the handpiece when the proximal portion of the hub is inserted into the receiving channel of the handpiece.

BRIEF DESCRIPTION OF THE DRAWINGS

Various embodiments of the present invention will now be discussed with reference to the appended drawings. It should be appreciated that the drawings depict only typical embodiments of the invention and are therefore not to be considered limiting in scope.

DETAILED DESCRIPTION OF THE INVENTION

The present invention relates to bone cutting and tissue removal devices and related methods of use. Several variations of the invention will now be described to provide an overall understanding of the principles of the form, function and methods of use of the devices disclosed herein. In general, the present disclosure provides for variations of arthroscopic tools adapted for cutting bone, soft tissue, meniscal tissue, and for RF ablation and coagulation. The arthroscopic tools are typically disposable and are configured for detachable coupling to a non-disposable handpiece that carries a motor drive component. This description of the general principles of this invention is not meant to limit the inventive concepts in the appended claims.

Figure 1:
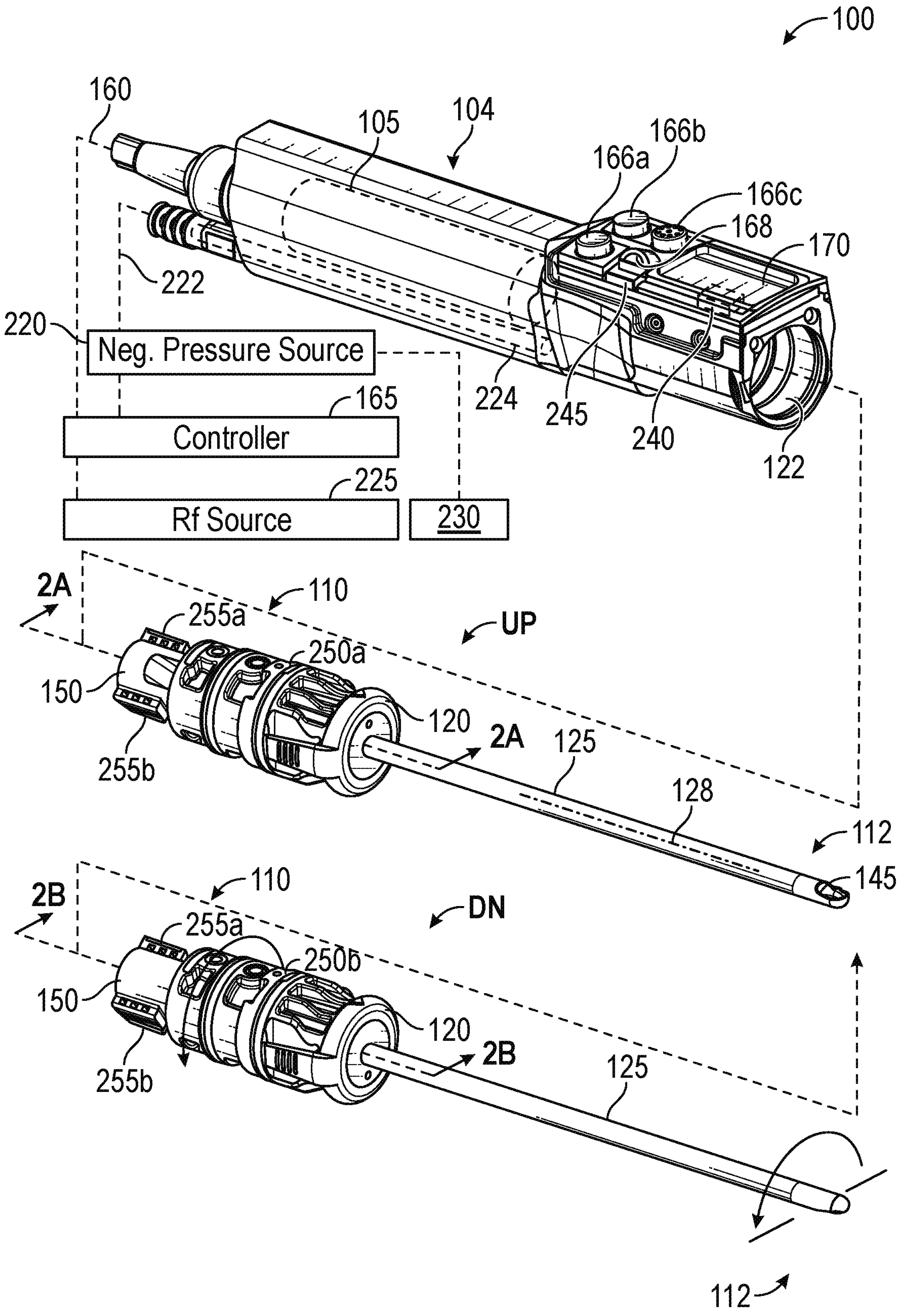
FIG. 1 is a perspective, exploded view of an arthroscopic cutting system that includes reusable handpiece with a motor drive and a detachable single-use cutting probe, wherein the cutting probe is shown in two rotational orientations relative a hub configured for removable attachment to the handpiece. Specifically, a working end of the probe is shown in upward orientation (UP) or a downward orientation (DN) relative to the hub and handpiece, and wherein the handpiece includes an LCD screen for displaying operating parameters of system during use together with control actuators on the handpiece.

In one variation shown in FIG. 1, the arthroscopic system 100 of the present invention provides a handpiece 104 with motor drive 105 and a disposable shaver assembly or probe 110 with a proximal hub 120 that can be received by receiver or bore 122 in the handpiece 104. In one aspect, the probe 110 has a working end 112 that carries a high-speed rotating cutter that is configured for use in many arthroscopic surgical applications, including but not limited to treating bone in shoulders, knees, hips, wrists, ankles and the spine.

Figure 2A:
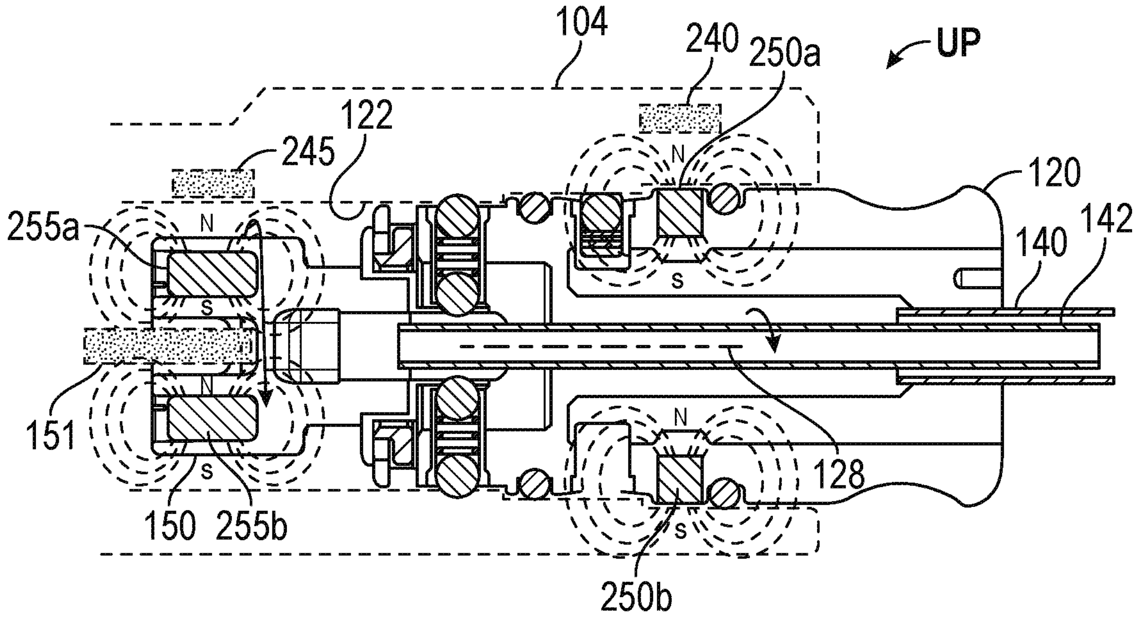
FIG. 2A is an enlarged longitudinal sectional view of the hub of the probe of FIG. 1 taken along line 2A-2A of FIG. 1 with the hub and probe in an upward orientation relative to the handpiece, further showing Hall effect sensors carried by the handpiece and a plurality of magnets carried by the probe hub for device identification, for probe orientation and determining the position of motor driven components of the probe relative to the handpiece.
Figure 3A:
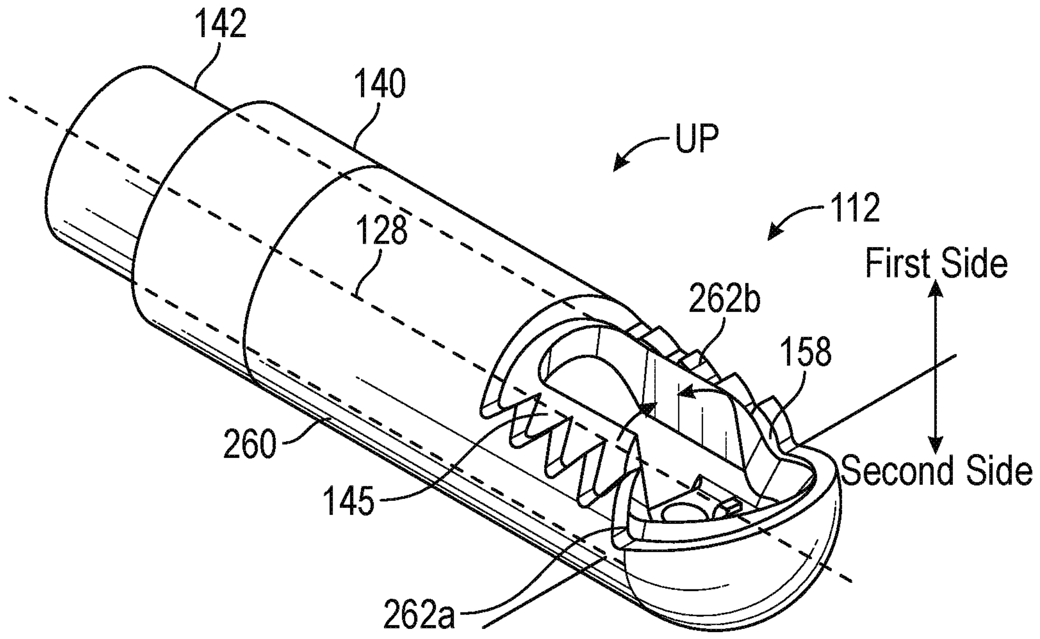
FIG. 3A is an enlarged perspective view of the working end of the probe of FIG. 1 in an upward orientation with the rotatable cutting member in a first position relative to the outer sleeve wherein the window in the cutting member is aligned with the window of the outer sleeve.
Figure 3B:
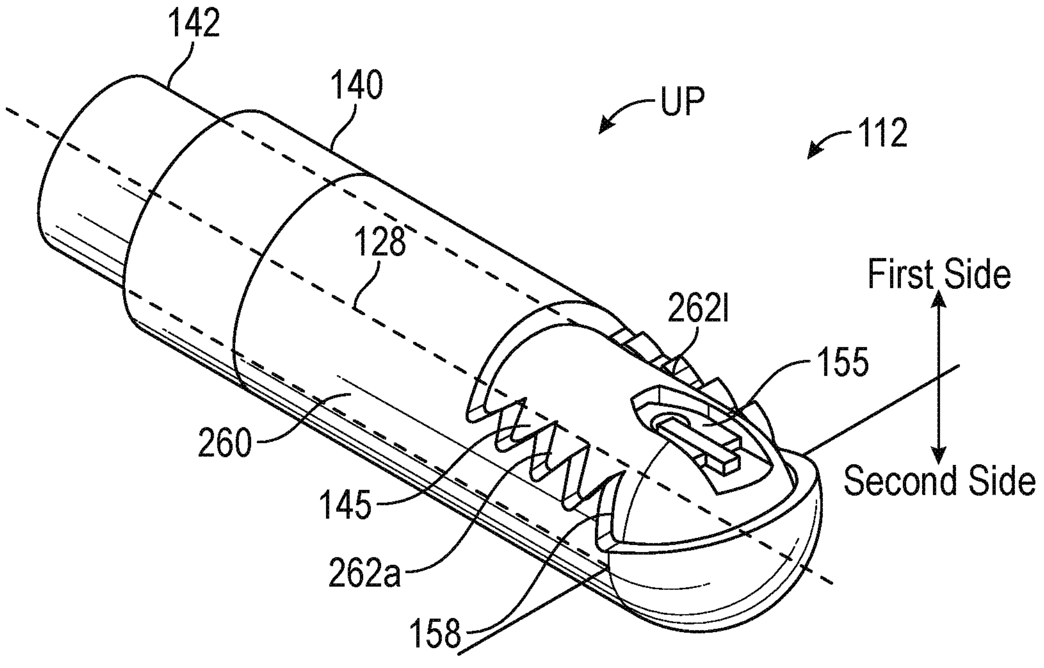
FIG. 3B is a perspective view of the working end of FIG. 1 in an upward orientation with the rotatable cutting member in a second position relative to the outer sleeve wherein the electrode carried by the cutting member is aligned with a centerline of the window of the outer sleeve.

In FIGS. 1, 2A and 3A, it can be seen that probe 110 has a shaft 125 extending along longitudinal axis 128 that comprises an outer sleeve 140 and an inner sleeve 142 rotatably disposed therein with the inner sleeve 142 carrying a distal ceramic cutting member 145 (FIG. 3A). The shaft 125 extends from the proximal hub 120 wherein the outer sleeve 140 is coupled in a fixed manner to the hub 120 which can be an injection molded plastic, for example, with the outer sleeve 140 insert molded therein. The inner sleeve 142 is coupled drive coupling 150 that is configured for coupling to the rotating motor shaft 151 of motor drive unit 105. More in particular, the rotatable cutting member 145 that is fabricated of a ceramic material with sharp cutting edges on opposing sides 152*a* and 152*b* of window 154 therein for cutting soft tissue. The motor drive 105 is operatively coupled to the ceramic cutter to rotate the cutting member at speeds ranging from 1,000 rpm to 20,000 rpm. In FIG. 3B, it can be seen that cutting member 145 also carries an RF electrode 155 in a surface opposing the window 154. The cutting member 145 rotates and shears tissue in the toothed opening or window 158 in the outer sleeve 140 (FIG. 3A). A probe of the type shown in FIG. 1 is described in more detail in co-pending and commonly owned patent application Ser. No. 15/421,264 filed Jan. 31, 2017, titled ARTHROSCOPIC DEVICES AND METHODS, which is incorporated herein in its entirety by this reference.

As can be seen in FIG. 1, the probe 110 is shown in two orientations for detachable coupling to the handpiece 104. More particularly, the hub 120 can be coupled to the handpiece 104 in an upward orientation indicated at UP and a downward orientation indicated at DN where the orientations are 180° opposed from one another. It can be understood that the upward and downward orientations are necessary to orient the working end 112 either upward or downward relative to the handpiece 104 to allow the physician to interface the cutting member 145 with targeted tissue in all directions without having to manipulate the handpiece in 360° to access tissue.

In FIG. 1, it can be seen that the handle 104 is operatively coupled by electrical cable 160 to a controller 165 which controls the motor drive unit 105 Actuator buttons 166*a*. 166*b* or 166*c* on the handle 104 can be used to select operating modes, such as various rotational modes for the ceramic cutting member 145. In one variation, a joystick 168 can be moved forward and backward to adjust the rotational speed of the ceramic cutting member 145. The rotational speed of the cutter can continuously adjustable, or can be adjusted in increments up to 20,000 rpm. An LCD screen 170 is provided in the handpiece for displaying operating parameters, such as cutting member RPM, mode of operation, etc.

Figure 4:
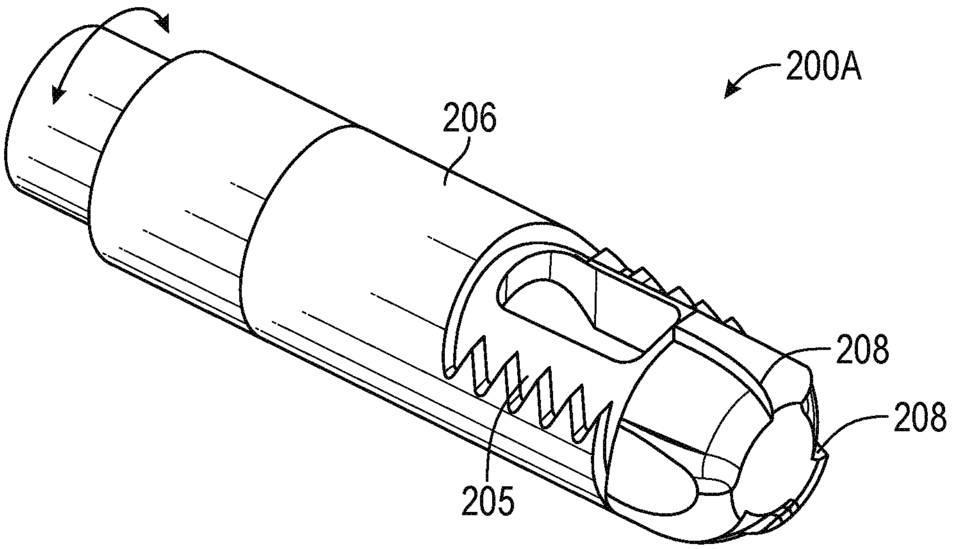
FIG. 4 is a perspective view of a working end of a variation of a probe that may be detachably coupled to the handpiece of FIG. 1, wherein the working end includes a bone burr extending distally from the outer sleeve.
Figure 5:
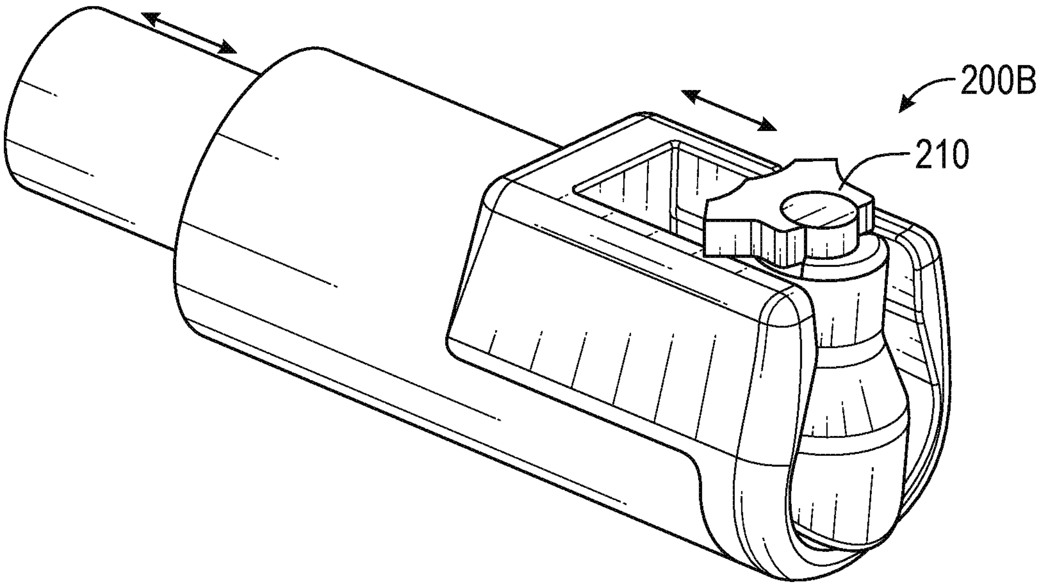
FIG. 5 is a perspective view of a working end of a variation of a probe that may be detachably coupled to the handpiece of FIG. 1, wherein the working end has a reciprocating electrode.
Figure 6:
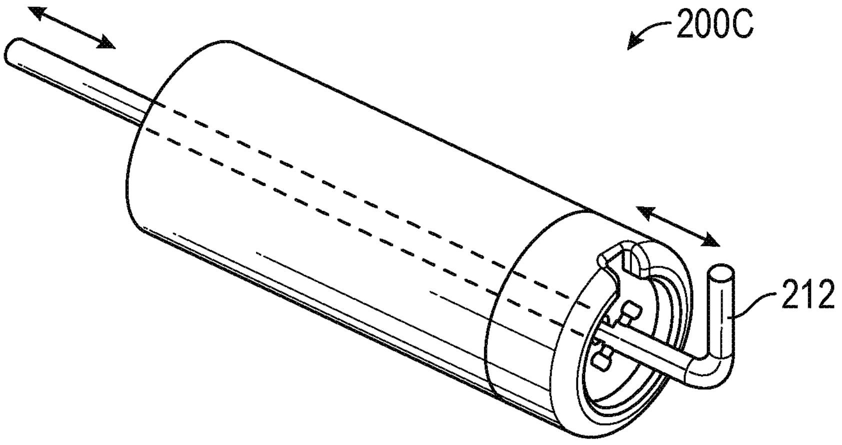
FIG. 6 is a perspective view of a working end of another variation of a probe that may be detachably coupled to the handpiece of FIG. 1, wherein the working end has a hook electrode that has extended and non-extended positions.
Figure 7:
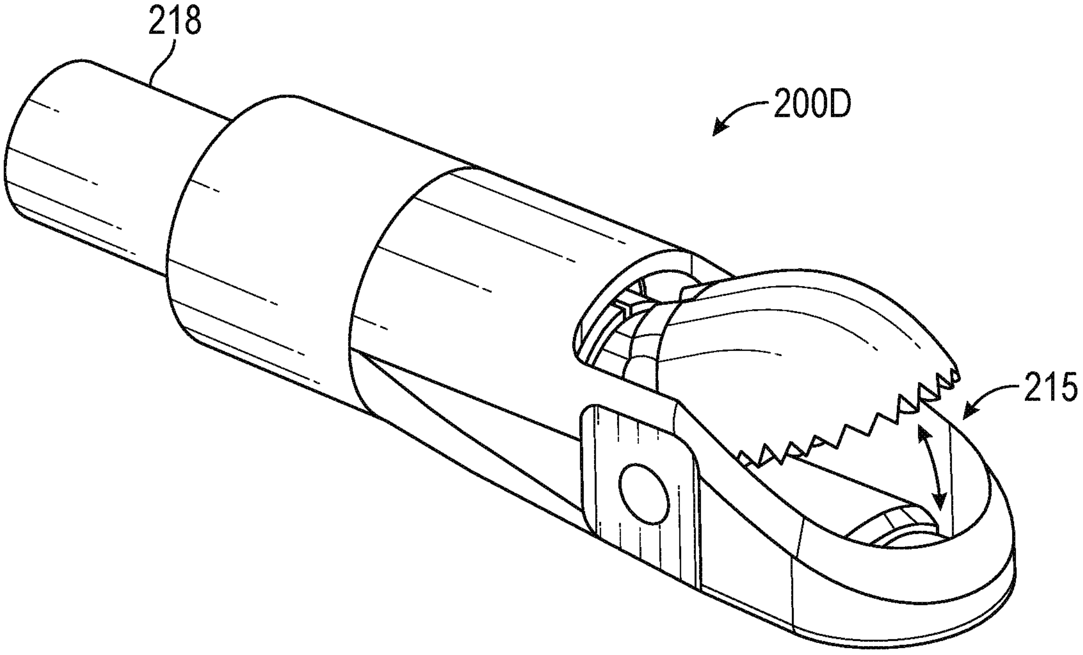
FIG. 7 is a perspective view of a working end of yet another variation of a probe that may be detachably coupled to the handpiece of FIG. 1, wherein the working end has an openable-closeable jaw structure for cutting tissue.

It can be understood from FIG. 1 that the system 100 and handpiece 104 is adapted for use with various disposable probes which can be designed for various different functions and procedures. For example, FIG. 4 illustrates a different variation of a probe working end 200A that is similar to working end 112 of probe 110 of FIGS. 3A-3B, except the ceramic cutting member 205 extends distally from the outer sleeve 206 and the cutting member has burr edges 208 for cutting bone. The probe of FIG. 4 is described in more detail in co-pending and commonly owned patent application Ser. No. 15/271,184 filed Sep. 20, 2016, titled ARTHROSCOPIC DEVICES AND METHODS. FIG. 5 illustrates a different variation of a probe working end 200B with a reciprocating electrode 210 in a type of probe described in more detail in co-pending and commonly owned patent application Ser. No. 15/410,723 filed Jan. 19, 2017, titled ARTHROSCOPIC DEVICES AND METHODS. In another example, FIG. 6 illustrates another variation of a probe working end 200C that has an extendable-retractable hook electrode 212 in a probe type described in more detail in co-pending and commonly owned patent application Ser. No. 15/454,342 filed Mar. 9, 2017, titled ARTHROSCOPIC DEVICES AND METHODS. In yet another example, FIG. 7 illustrates a variation of a working end 200D in a probe type having an openable-closable jaw, structure 215 actuated by reciprocating member 218 for trimming meniscal tissue or other tissue as described in more detail in co-pending and commonly owned patent application Ser. No. 15/483,940 filed Apr. 10, 2017, titled ARTHROSCOPIC DEVICES AND METHODS. All of the probes of FIGS. 4-7 can have a hub similar to hub 120 of probe 110 of FIG. 1 for coupling to the same handpiece 104 of FIG. 1, with some of the probes (see FIGS. 5-7) having a hub mechanism for converting rotational motion to linear motion. All of the patent applications just identified in this paragraph are incorporated herein by this reference.

FIG. 1 further shows that the system 100 also includes a negative pressure source 220 coupled to aspiration tubing 222 which communicates with a flow channel 224 in handpiece 104 and can cooperate with any of the probes 110, 200A, 200B or 200C of FIGS. 1-3B, 4, 5 and 6. In FIG. 1 it also can be seen that the system 100 includes an RF source 225 which can be connected to an electrode arrangement in any of the probes 110, 200A, 200B or 200C of FIGS. 1-3B, 4, 5 and 6. The controller 165 and microprocessor therein together with control algorithms are provided to operate and control all functionality, which includes controlling the motor drive 105 to move a motor-driven component of any probe working end 110, 200A, 200B or 200C, as well as for controlling the RF source 225 and the negative pressure source 220 which can aspirate fluid and tissue debris to collection reservoir 230.

As can be understood from the above description of the system 100 and handpiece 104, the controller 165 and controller algorithms need to be configured to perform and automate many tasks to provide for system functionality. In a first aspect, controller algorithms are needed for device identification so that when any of the different probes types 110, 200A, 200B, 200C or 200D of FIGS. 1 and 4-7 are coupled to handpiece 104, the controller 165 will recognize the probe type and then select algorithms for operating the motor drive 105, RF source 225 and negative pressure source 220 as is needed for the particular probe. In a second aspect, the controller is configured with algorithms that identify whether the probe is coupled to the handpiece 104 in an upward or downward orientation relative to the handpiece, wherein each orientation requires a different subset of the operating algorithms. In another aspect, the controller has separate control algorithms for each probe type wherein some probes have a rotatable cutter while others have a reciprocating electrode or jaw structure. In another aspect, most if not all the probes 110, 200A, 200B, 200C and 200D (FIGS. 1, 4-7) require a default "stop" position in which the motor-driven component is stopped in a particular orientation within the working end. For example, a rotatable cutter 145 with an electrode 155 needs to have the electrode centered within an outer sleeve window 158 in a default position such as depicted in FIG. 3B. Some of these systems, algorithms and methods of use are described next.

Figure 2B:
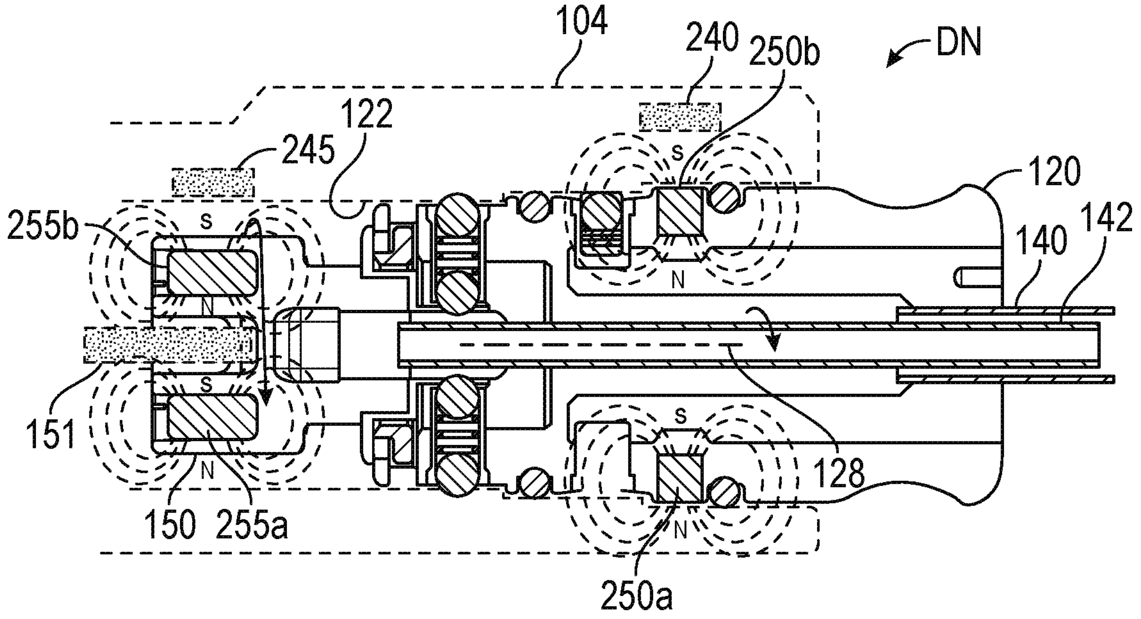
FIG. 2B is a sectional view of the hub of FIG. 1 taken along line 2B-2B of FIG. 1 with the hub and probe in a downward orientation relative to the handpiece showing the Hall effect sensor and magnets having a different orientation compared to that of FIG. 2A.

Referring to FIGS. 1 and 2A-2B, it can be seen that handpiece 104 carries a first Hall effect sensor 240 in a distal region of the handpiece 104 adjacent the receiving passageway 122 that receives the hub 120 of probe 110. FIG. 2A corresponds to the probe 110 and working end 112 in FIG. 1 being in the upward orientation indicated at UP. FIG. 2B corresponds to probe 110 and working end 112 in FIG. 1 being in the downward orientation indicated at DN. The handpiece 104 carries a second Hall effect sensor 245 adjacent the rotatable drive coupling 150 of the probe 110. The probe 110 carries a plurality of magnets as will be described below that interact with the Hall effect sensors 240, 245 to provide multiple control functions in cooperation with controller algorithms, including (i) identification of the type of probe coupled to the handpiece, (ii) the upward or downward orientation of the probe hub 120 relative to the handpiece 104, and (iii) the rotational position and speed of rotating drive collar 150 from which a position of either rotating or reciprocating motor-driven components can be determined.

The sectional views of FIGS. 2A-2B show that hub 120 of probe 110 carries first and second magnets 250*a* and 250*b* in a surface portion thereof. The Hall sensor 240 in handpiece 104 is in axial alignment with either magnet 250*a* or 250*b* when the probe hub 120 is coupled to handpiece 104 in an upward orientation (FIGS. 1 and 2A) or a downward orientation (FIGS. 1 and 2B). In one aspect as outlined above, the combination of the magnets 250*a* and 250*b* and the Hall sensor 240 can be used to identify the probe type. For example, a product portfolio may have from 2 to 10 or more types of probes, such as depicted in FIGS. 1 and 4-7, and each such probe type can carry magnets 250*a*, 250*b* having a specific, different magnetic field strength. Then, the Hall sensor 240 and controller algorithms can be adapted to read the magnetic field strength of the particular magnet(s) in the probe which can be compared to a library of field strengths that correspond to particular probe types. Then, a Hall identification signal can be generated or otherwise provided to the controller 165 to select the controller algorithms for operating the identified probe, which can include parameters for operating the motor drive 105, negative pressure source 220 and/or RF source 225 as may be required for the probe type. As can be seen in FIGS. 1, 2A and 2B, the probe hub 120 can be coupled to handpiece 104 in upward and downward orientations, in which the North (N) and South (S) poles of the magnets 250*a*, 250*b* are reversed relative to the probe axis 128. Therefore, the Hall sensor 240 and associated algorithms look for magnetic field strength regardless of polarity to identify the probe type.

Referring now to FIGS. 1, 2A-2B and 3A-3B, the first and second magnets 250*a* and 250*b* with their different orientations of North (N) and South (S) poles relative to central longitudinal axis 128 of hub 120 are also used to identify the upward orientation UP or the downward orientation DN of hub 120 and working end 112. In use, as described above, the physician may couple the probe 110 to the handpiece receiving passageway 122 with the working end 112 facing upward or downward based on his or her preference and the targeted tissue. It can be understood that controller algorithms adapted to stop rotation of the cutting member 145 in the window 158 of the outer sleeve 104 of working end 112 need to "learn" whether the working end is facing upward or downward, because the orientation or the rotating cutting member 145 relative to the handpiece and Hall sensor 240 would vary by 180°. The Hall sensor 240 together with a controller algorithm can determine the orientation UP or the downward orientation DN by sensing whether the North (N) or South (S) pole of either magnet 250*a* or 250*b* is facing upwardly and is proximate the Hall sensor 240.

In another aspect of the invention, in probe 110 (FIG. 1) and other probes, the motor-driven component of a working end, such as rotating cutter 145 of working end 112 of FIGS. 1 and 3A-3B needs to be stopped in a selected rotational position relative to a cut-out opening or window 158 in the outer sleeve 140. Other probe types may have a reciprocating member or a jaw structure as described above, which also needs a controller algorithm to stop movement of a moving component in a selected position, such as the axial-moving electrodes of FIGS. 5-6 and the jaw structure of FIG. 7. In all probes, the motor drive 105 couples to the rotating drive coupling 150, thus sensing the rotational position of the drive coupling 150 can be used to determine the orientation of the motor-driven component in the working end. More in particular, referring to FIGS. 1 and 2A-2B, the drive coupling 150 carries third and fourth magnets 255*a* or 255*b* with the North (N) and South (S) poles of magnets 255*a* or 255*b* being reversed relative to the probe axis 128. Thus, Hall sensor 245 can sense when each magnet rotates passes the Hall sensor and thereby determine the exact rotational position of the drive coupling 150 twice on each rotation thereof (once for each magnet 255*a*, 255*b*). Thereafter, a controller tachometer algorithm using a clock can determine and optionally display the RPM of the drive coupling 150 and, for example, the cutting member 145 of FIG. 3A.

In another aspect of the invention, the Hall sensor 245 and magnets 255*a* and 255*b* (FIGS. 1 and 2A) are used in a set of controller algorithms to stop the rotation of a motor-driven component of a working end, for example, cutting member 145 of FIGS. 1 and 3A-3B in a pre-selected rotational position. In FIG. 3A, it can be seen that the inner sleeve 142 and a "first side" of cutting member 145 and window 154 therein is stopped and positioned in the center of window 158 of outer sleeve 140. The stationary position of cutting member 145 and window 154 in FIG. 3A may be used for irrigation or flushing of a working space to allow for maximum fluid outflow through the probe.

FIG. 3B depicts inner sleeve 142 and a "second side" of cutting member 145 positioned about the centerline of window 158 in the outer sleeve 140. The stationary or stopped position of cutting member 145 in FIG. 3B is needed for using the RF electrode 155 to ablate or coagulate tissue. It is important that the electrode 155 is maintained along the centerline of the outer sleeve window 158 since the outer sleeve 140 typically comprises return electrode 260. The position of electrode 155 in FIG. 3B is termed herein a "centerline default position." If the cutting member 145 and electrode 155 were rotated so as to be close to an edge 262*a* or 262*b* of window 158 in outer sleeve 140, RF current could arc between the electrodes 155 and 260 and potentially cause a short circuit disabling the probe. Therefore, a robust and reliable stop mechanism is required which is described next.

As can be understood from FIGS. 1 and 2A-2B, the controller 165 can always determine in real time the rotational position of drive coupling 150 and therefore the angular or rotational position of the ceramic cutting member 145 and electrode 155 can be determined. A controller algorithm can further calculate the rotational angle of the electrode 155 away from the centerline default position as the Hall sensor 245 can sense lessening of magnetic field strength as a magnet 255*a* or 255*b* in the drive coupling 150 rotates the electrode 155 away from the centerline default position. Each magnet has a specified, known strength and the algorithm can use a look-up table with that lists fields strengths corresponding to degrees of rotation away from the default position. Thus, if the Hall signal responsive to the rotated position of magnet 255*a* or 255*b* drops a specified amount from a known peak value in the centerline default position, it means the electrode 155 has moved away from the center of the window 158. In one variation, if the electrode 155 moves a selected rotational angle away from the centerline position during RF energy delivery to the electrode, the algorithm turns off RF current instantly and alerts the physician by an aural and/or visual signal, such as an alert on the LCD screen 170 on handpiece 104 and/or on a screen on a controller console (not shown). The termination of RF current delivery thus prevents the potential of an electrical arc between electrode 155 and the outer sleeve electrode 260.

It can be understood that during use, when the electrode 155 is in the position shown in FIG. 3B, the physician may be moving the energized electrode over tissue to ablate or coagulate tissue. During such use, the cutting member 145 and electrode 155 can engage or catch on tissue which inadvertently rotate the electrode 155 out of the default centerline position. Therefore, the system provides a controller algorithm, herein called an "active electrode monitoring" algorithm, wherein the controller continuously monitors position signals generated by Hall sensor 245 during RF energy delivery in both an ablation mode and a coagulation mode to determine if the electrode 155 and inner sleeve 142 have been bumped off the centerline position. In a variation, the controller algorithms can be configured to then re-activate the motor drive 105 to move the inner sleeve 142 and electrode 155 back to the default centerline position sleeve if electrode 155 had been bumped off the centerline position. In another variation, the controller algorithms can be configured to again automatically deliver RF current to RF electrode 155 when it is moved back to the to the default centerline position. Alternatively, the controller 165 can require the physician to manually re-start the delivery of RF current to the RF electrode 155 when it is moved back to the to the centerline position. In an aspect of the invention, the drive coupling 150 and thus magnets 255*a* and 255*b* are attached to inner sleeve 142 and cutting member 145 in a pre-determined angular relationship relative to longitudinal axis 128 so that the Hall sensor generates signals responsive to magnets 255*a*, 255*b* is the same for all probes within a probe type to thus allow the controller algorithm to function properly.

Figure 8:
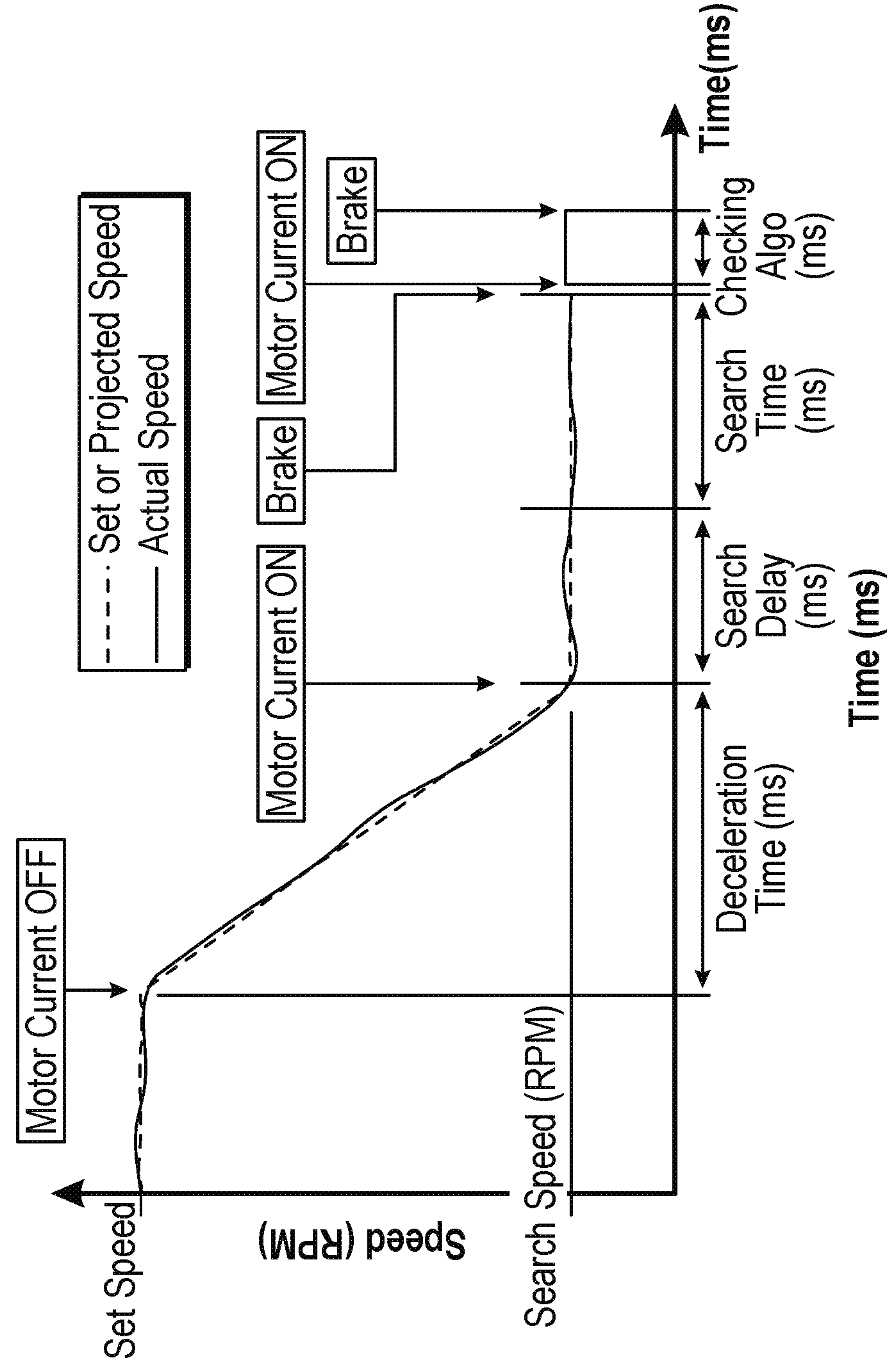
FIG. 8 is a chart relating to set speeds for a probe with a rotating cutting member as in FIGS. 1 and 3A that schematically shows the method used by a controller algorithm for stopping rotation of the cutting member in a selected default position.

Now turning to the stop mechanism or algorithms for stopping movement of a motor-driven component of working end 112, FIG. 8 schematically illustrates the algorithm and steps of the stop mechanism. In one variation, referring to FIG. 8, the stop mechanism corresponding to the invention uses (i) a dynamic braking method and algorithm to stop the rotation of the inner sleeve 142 and cutting member 145 (FIGS. 1, 3A-3B) in an initial position, and thereafter (ii) a secondary checking algorithm is used to check the initial stop position that was attained with the dynamic braking algorithm, and if necessary, the stop algorithm can re-activate the motor drive 105 to slightly reverse (or move forward) the rotation of drive coupling 150 and inner sleeve 142 as needed to position the cutting member 145 and electrode 155 within at the centerline position or within 0° to 5° of the targeted centerline default position. Dynamic braking is described further below. FIG. 8 schematically illustrates various aspects of controller algorithms for controlling the rotational speed of the cutting member and for stopping the cutting member 145 in the default centerline position.

In FIG. 8, it can be understood that the controller 165 is operating the probe 110 of FIGS. 1 and 3A-3B at a "set speed" which may be a PID controlled, continuous rotation mode in one direction or may be an oscillating mode where the motor drive 105 rotates the cutting member 145 in one direction and then reverses rotation as is known in the art. At higher rotational speeds such as 1,000 RPM to 20,000 RPM, it is not practical or feasible to acquire a signal from Hall sensor 245 that indicates the position of a magnet 255*a* or 255*b* in the drive coupling 150 to apply a stop algorithm. In FIG. 8, when the physician stop cutting with probe 110 by releasing actuation of an actuator button or foot pedal, current to the motor drive 105 is turned off Thereafter, the controller algorithm uses the Hall sensor 245 to monitor deceleration of rotation of the drive coupling 150 and inner sleeve 142 until a slower RPM is reached. The deceleration period may be from 10 ms to 1 sec and typically is about 100 ms. When a suitable slower RPM is reached which is called a "search speed" herein (see FIG. 8), the controller 165 re-activates the motor drive 105 to rotate the drive coupling at a low speed ranging from 10 RPM to 1,000 RPM and in one variation is between 50 RPM and 250 RPM. An initial "search delay" period ranging from 50 ms to 500 ms is provided to allow the PID controller to stabilize the RPM at the selected search speed. Thereafter, the controller algorithm monitors the Hall position signal of magnet strength and when the magnet parameter reaches a predetermined threshold, for example, when the rotational position of drive coupling 150 and electrode 155 correspond to the centerline default position of FIG. 3B, the control algorithm then applies dynamic braking to instantly stop rotation of the motor drive shaft 151, drive coupling 150 and the motor-driven component of the probe. FIG. 8 further illustrates that the controller can check the magnet/drive coupling 150 position after the braking and stopping steps. If the Hall position signal indicates that the motor-driven component is out of the targeted default position, the motor drive 105 can be re-activated to move the motor-driven component and thereafter the brake can be applied again as described above.

Dynamic braking as shown schematically in FIG. 8 may typically stop the rotation of the drive coupling 150 with a variance of up to about 0°-15° of the targeted stop position, but this can vary even further when different types of tissue are being cut and impeding rotation of the cutting member 145, and also depending on whether the physician has completely disengaged the cutting member from the tissue interface when the motor drive is de-activated. Therefore, dynamic braking alone may not assure that the default or stop position is within a desired variance.

As background, the concept of dynamic braking is described in the following literature: https://www.ab.com/support/abdrives/documentation/techpapers/RegenOverview01.pdf and http://literature.rockwellautomation.com/idc/groups/literature/documents/wp/drives-wp004_-en-p.pdf. Basically, a dynamic braking system provides a chopper transistor on the DC bus of the AC PWM drive that feeds a power resistor that transforms the regenerative electrical energy into heat energy. The heat energy is dissipated into the local environment. This process is generally called dynamic braking with the chopper transistor and related control and components called the chopper module and the power resistor called the dynamic brake resistor. The entire assembly of chopper module with dynamic brake resistor is sometimes referred to as the dynamic brake module. The dynamic brake resistor allows any magnetic energy stored in the parasitic inductance of that circuit to be safely dissipated during the turn off of the chopper transistor.

The method is called dynamic braking because the amount of braking torque that can be applied is dynamically changing as the load decelerates. In other words, the braking energy is a function of the kinetic energy in the spinning mass and as it declines, so does the braking capacity. So the faster it is spinning or the more inertia it has, the harder you can apply the brakes to it, but as it slows, you run into the law of diminishing returns and at some point, there is no longer any braking power left.

In another aspect of the invention, a method has been developed to increase the accuracy of the stopping mechanism which is a component of the positioning algorithm described above. It has been found that each magnet in a single-use probe may vary slightly from its specified strength. As described above, the positioning algorithm uses the Hall effect sensor 245 to continuously monitor the field strength of magnets 255*a* and 255*b* as the drive coupling 150 rotates and the algorithm determines the rotational position of the magnets and drive coupling based on the field strength, with the field strength rising and falling as a magnet rotates past the Hall sensor. Thus, it is important for the algorithm to have a library of fields strengths that accurately correspond to degrees of rotation away from a peak Hall signal when a magnet is adjacent the sensor 245. For this reason, an initial step of the positioning algorithm includes a "learning" step that allow the controller to learn the actual field strength of the magnets 255*a* and 255*b* which may vary from the specified strength. After a new single-use probe 110 (FIG. 1) is coupled to the handpiece 104, and after actuation of the motor drive 105, the positioning algorithm will rotate the drive coupling at least 180° and more often at least 360° while the Hall sensor 245 quantifies the field strength of the particular probe's magnets 255*a* and 255*b*. The positioning algorithm then stores the maximum and minimum Hall signals (corresponding to North and South poles) and calibrates the library of field strengths that correspond to various degrees of rotation away from a Hall min-max signal position when a magnet is adjacent the Hall sensor.

In general, a method of use relating to the learning algorithm comprises providing a handpiece with a motor drive, a controller, and a probe with a proximal hub configured for detachable coupling to the handpiece, wherein the motor drive is configured to couple to a rotating drive coupling in the hub and wherein the drive coupling carries first and second magnets with North and South poles positioned differently relative to said axis, and coupling the hub to the handpiece, activating the motor drive to thereby rotate the drive coupling and magnets at least 180°, using a handpiece sensor to sense the strength of each magnet, and using the sensed strength of the magnets for calibration in a positioning algorithm that is responsive to the sensor sensing the varying strength of the magnets in the rotating drive coupling to thereby increase accuracy in calculating the rotational position of the drive coupling 150.

Another aspect of the invention relates to an enhanced method of use using a probe working end with an electrode, such as the working end 112 of FIGS. 1 and 3B. As described above, a positioning algorithm is used to stop rotation of the electrode 155 in the default centerline position of FIG. 3B. An additional "slight oscillation" algorithm is used to activate the motor drive 105 contemporaneous with RF current to the electrode 155, particularly an RF cutting waveform for tissues ablation. The slight oscillation thus provides for a form of oscillating RF ablation. The slight oscillation algorithm rotates the electrode 155 in one direction to a predetermined degree of rotation, which the controller algorithms determine from the Hall position signals. Then, the algorithm reverses direction of the motor drive to rotate in the opposite direction until Hall position signals indicate that the predetermined degree of rotation was achieved in the opposite direction away from the electrode's default centerline position. The predetermined degree of angular motion can be any suitable rotation that is suitable for dimensions of the outer sleeve window, and in one variation is from 1° to 30° in each direction away from the centerline default position. More often, the predetermined degree of angular motion is from 5° to 15° in each direction away from the centerline default. The slight oscillation algorithm can use any suitable PID controlled motor shaft speed, and in one variation the motor shaft speed is from 50 RPM to 5,000 RPM, and more often from 100 RPM to 1,000 RPM. Stated another way, the frequency of oscillation can be from 20 Hz to 2,000 Hz and typically between 40 Hz and 400 Hz.

While the above description of the slight oscillation algorithm is provided with reference to electrode 155 on a rotating cutting member 145 of FIG. 3B, it should be appreciated that a reciprocating electrode 212 as shown in the working end 200C of FIG. 6 end could also be actuated with slight oscillation. In other words, the hook shape electrode 212 of FIG. 6 could be provided with a frequency of oscillation ranging from 20 Hz to 2,000 Hz and typically between 40 Hz and 400 Hz.

Figure 9A:
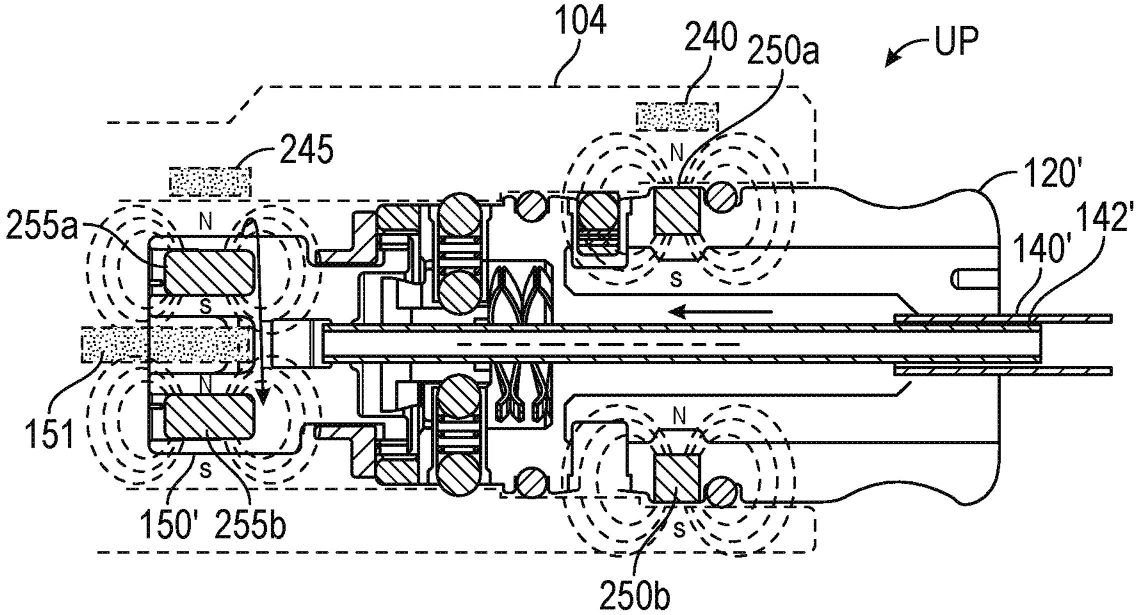
FIG. 9A is a longitudinal sectional view of a probe hub that is similar to that of FIG. 2A, except the hub of FIG. 9A has an internal cam mechanism for converting rotational motion to linear motion to axially reciprocate an electrode as in the working end of FIG. 5, wherein FIG. 9A illustrated the magnets in the hub and drive coupling are the same as in FIG. 2A and the hub is in an upward facing position relative to the handpiece.
Figure 9B:
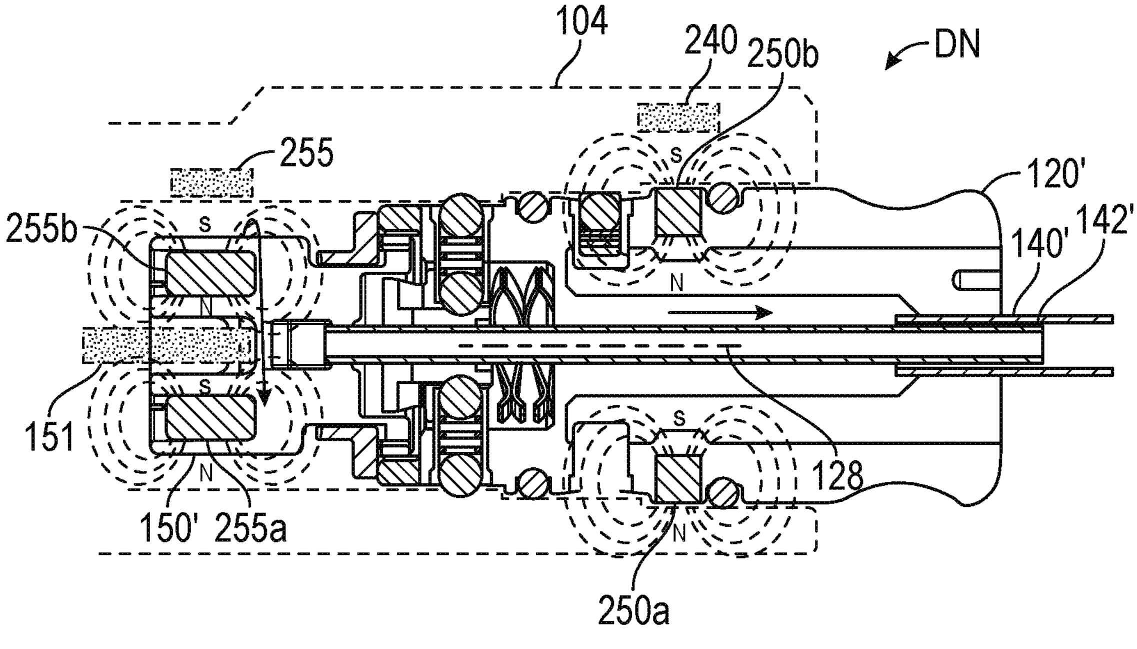
FIG. 9B is a sectional view of the hub of FIG. 9A rotated 180° in a downward facing position relative to the handpiece.

FIGS. 9A-9B are longitudinal sectional views of a probe hub 120' that corresponds to the working end 200B of FIG. 5 which has a reciprocating electrode 210. In FIGS. 9A-9B, the handpiece 104 and Hall affect sensors 240 and 245 are of course the same as described above as there is no change in the handpiece 104 for different types of probes. The probe hub 120' of FIGS. 9A-9B is very similar to the hub 120 of FIGS. 2A-2B with the first and second identification/orientation magnets 250*a* and 250*b* being the same. The third and fourth rotation al position magnets 255*a* and 255*b* also are the same and are carried by drive coupling 150'. The probe hub 120' of FIGS. 9A-9B only differs in that the drive coupling 150 rotates with a cam mechanism operatively coupled to inner sleeve 142' to convert rotational motion to linear motion to reciprocate the electrode 210 in working end 200B of FIG. 5. A similar hub for converting rotational motion to linear motion is provided for the working ends 200C and 200D of FIGS. 6 and 7, respectively, which each have a reciprocating component (212, 218) in its working end.

Figure 10:
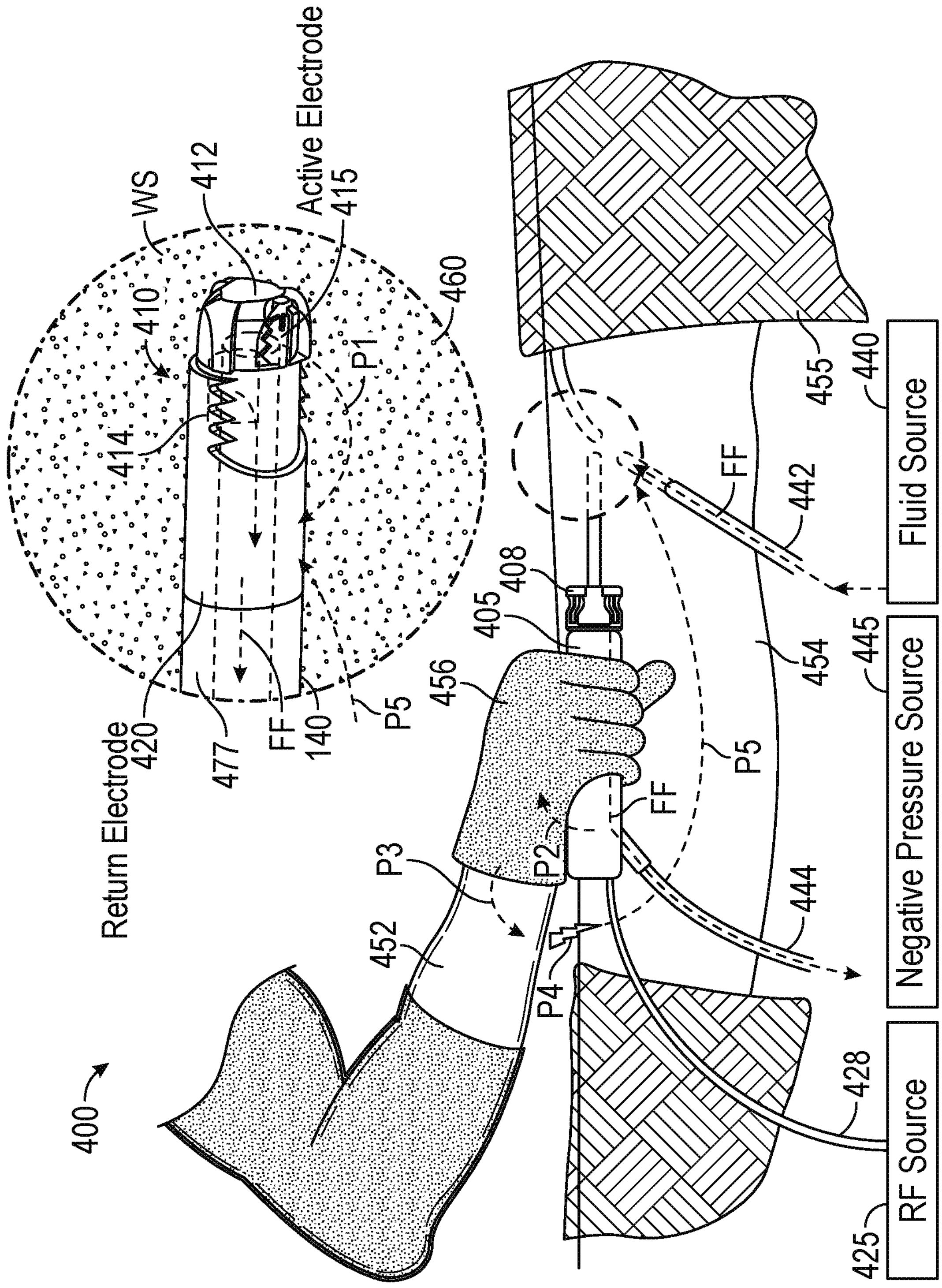
FIG. 10 is a schematic illustration of a procedure in which a physician holds the arthroscopic probe while treating the patient's knee and wherein the potential exists for capacitive coupling from the handpiece to the physician's un-draped arm and then to the patient's un-draped leg which can cause an electrical shock or burn on the physician's arm and the patient's leg, with the illustration showing potential RF current paths between the active and return electrodes carried by the probe working end.

Now turning to FIGS. 10 and 11A-11C, other aspects of the invention are illustrated that relate to controlling inadvertent RF current paths in the saline flowing through the probe from a working space WS. FIG. 10 schematically illustrates an arthroscopic system 400 in use wherein a surgeon grips a handpiece 405 with the arthroscopic cutting and ablation probe 408 coupled thereto. The probe 408 is of the type shown in FIGS. 1 and 3A-3B with a working end 410 shown in an enlarged view in the bubble of FIG. 10. The working end 410 comprises a rotating dielectric or ceramic cutter 412 that carries an active electrode 415 as described previously. An aspiration window 414 is provided in the ceramic cutter 412. The outer sleeve 140 (see FIG. 3A) carries a return electrode 420 as in the variation of FIGS. 3A-3B. The arthroscopic system 400 further includes an RF source 425 coupled to the handpiece 405 and probe 408 with electrical cable 428. The arthroscopic system 400 further includes a fluid source 440 that provides for fluid flows FF through an introducer 442 into the working space WS together with a negative pressure source 445 coupled to the handle which sections are aspirates fluid from the working space through the probe 408, the handpiece 405 and the aspiration tubing 444.

Figure 11A:
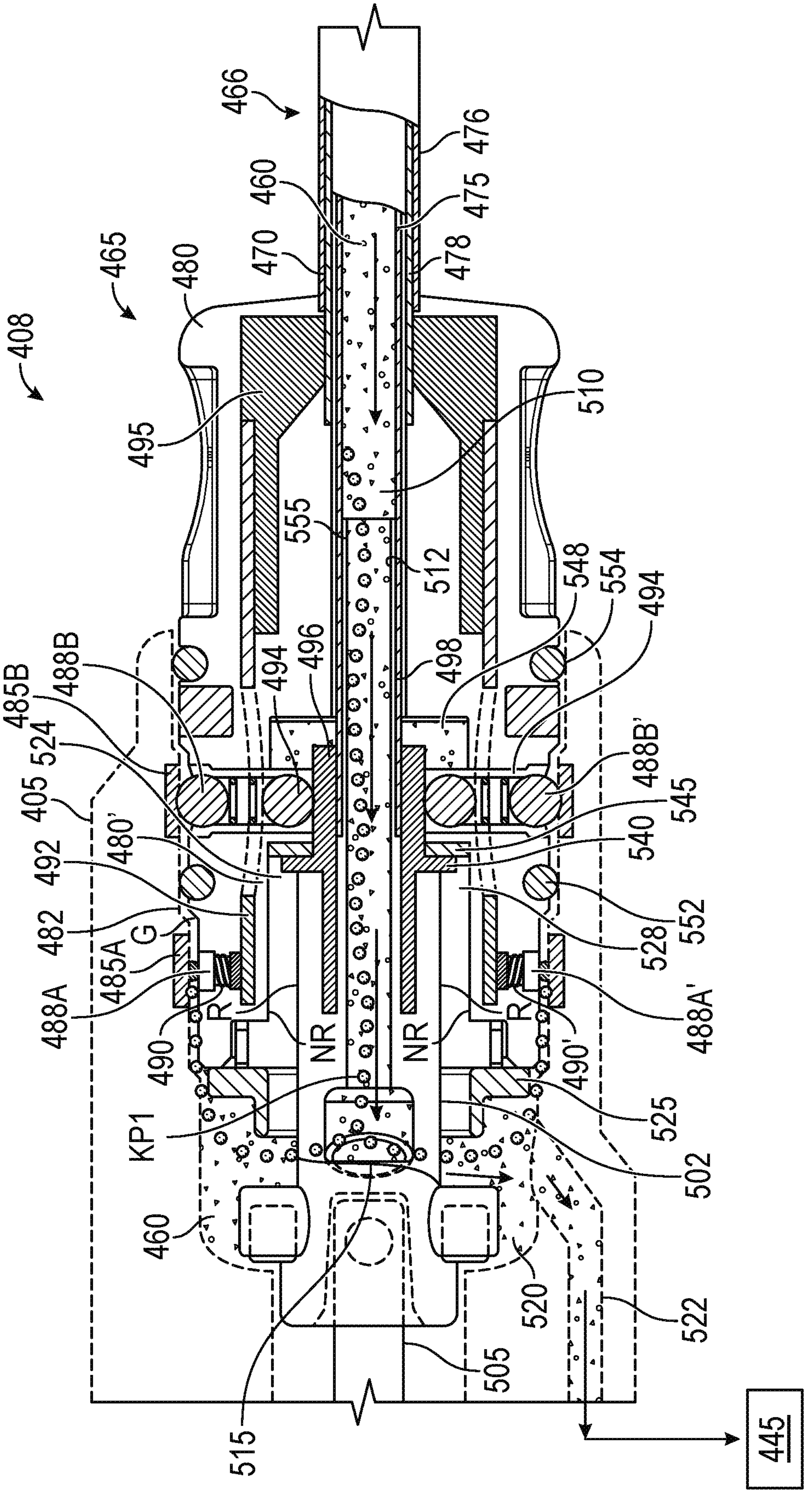
FIG. 11A is sectional view of the of hub of the arthroscopic probe of FIG. 10 showing components and features of the hub that control RF current flows through a first potential path in the interior of the hub through the saline outflow.
Figure 11B:
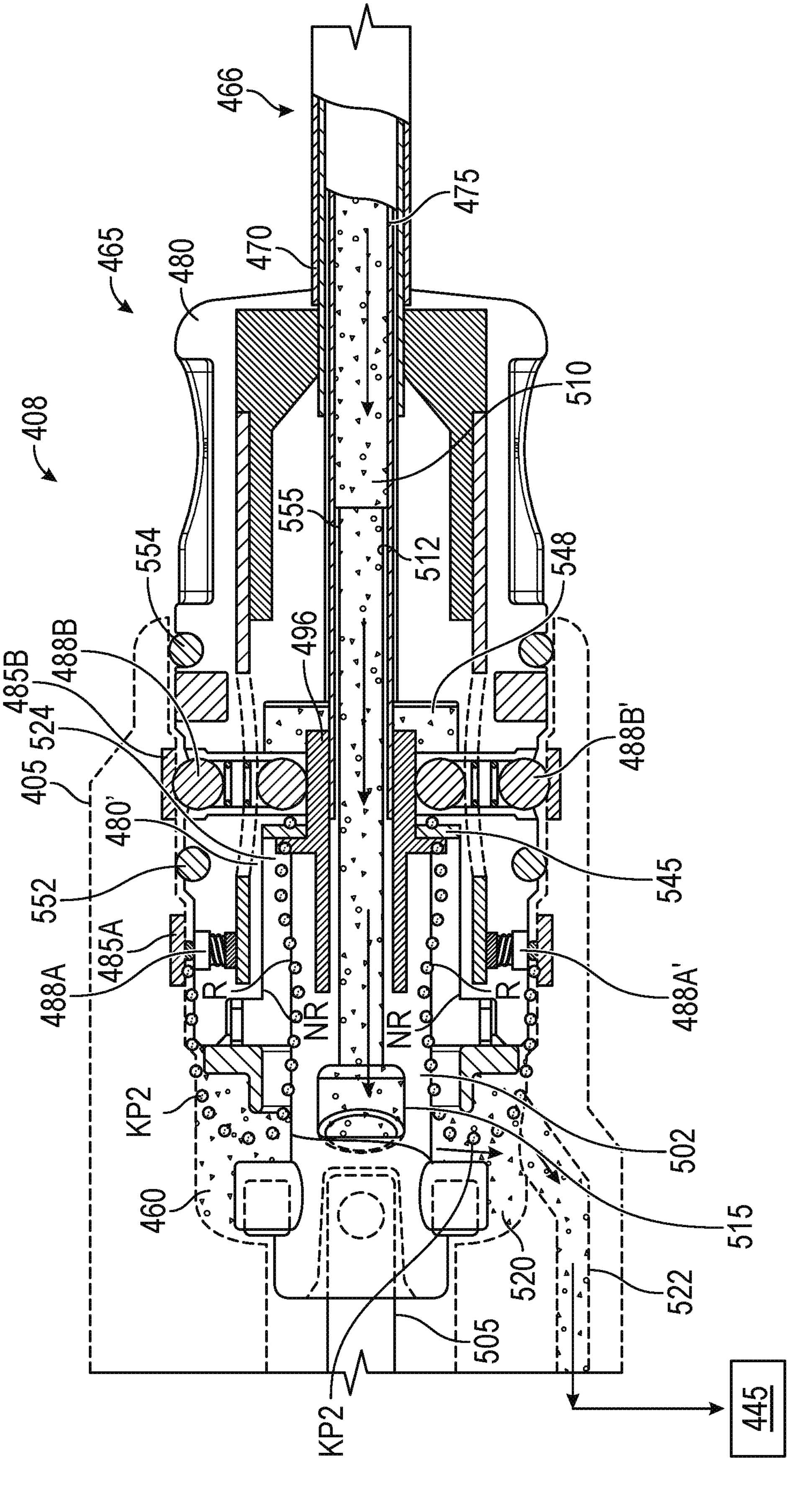
FIG. 11B is sectional view of the probe hub of FIG. 11A showing features of the hub that prevent or limit RF current flow through second potential inadvertent flow paths in the hub.
Figure 11C:
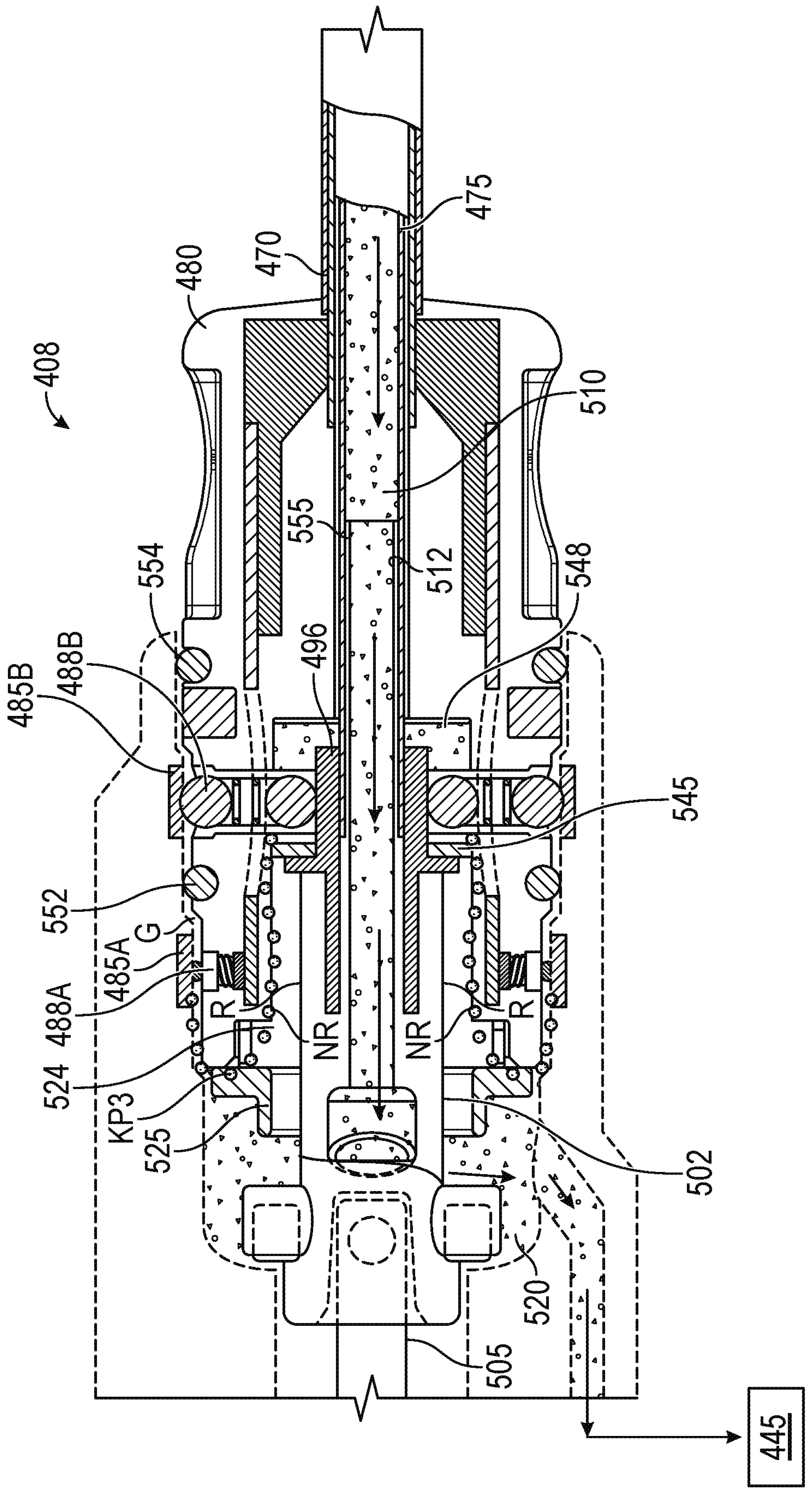
FIG. 11C is sectional view of the probe hub of FIG. 11A showing features of the hub that prevent or limit RF current flow through third potential inadvertent flow paths in the hub.

In FIG. 10, the components of the arthroscopic system 400 together with fluid inflow and fluid outflow paths are shown to further describe the potential RF current paths. FIGS. 11A-11C will describe components in the handpiece 405 and the probe 408 that are designed to reduce or eliminate the risk of inadvertent RF current paths coupling to the arm 452 of the surgeon which under certain circumstances could cause a shock a burn on the arm 452 of the surgeon or and/or the leg 454 of the patient.

Still referring to FIG. 10, it can be understood that in a typical arthroscopic procedure, the patient's leg 454 and knee would be covered with a drape 455 which also would be an electrically insulating material. Obviously, portion of the patient's leg 454 and knee is not draped. As also shown in FIG. 10, the surgeon would be wearing electrically insulating gloves 456 and a gown 458. However, it is possible that a portion of the physician's arm 452 may be uncovered as shown in FIG. 10.

FIG. 10 shows the working end 410 of the probe 408 in an enlarged view in a working space WS that is infused with conductive saline 460 from fluid source 440. In the enlarged view of the working end 410 of FIG. 10, the active electrode 415 and return electrode 420 are shown with a typical RF current path P1 through the saline 460 between the electrodes.

In FIG. 10, it can be further understood that the negative pressure source 445 suctions fluid or saline 460 from the working space WS through the probe 408 and through the handpiece 405 to a collection reservoir (not shown). Thus, it can be understood that RF current in the working space WS also carries electrical potential through the column of conductive saline 460 being suctioned from the working space WS through the probe 408 and handpiece 405 by the negative pressure source 445. FIG. 10 illustrates a potential inadvertent RF current path that extends from the active electrode 415 in the working space WS through the column of saline 460 to the return electrode 420. Such an inadvertent RF current path starts in the fluid flow FF through the handpiece 405, then capacitively couples through the surgeon's glove 456 into the arm of the surgeon indicated at RF current path P2, then through the arm 452 of the surgeon indicated at current path P3, then in an arc or current path P4 between the surgeon's arm 452 and the patient's leg 454, and then finally through the current path PS through the patient's leg 454 to the return electrode 420 in the working space WS. This circuitous potential RF current path might only occur in the unique circumstances where the surgeon's arm 452 is exposed, however if RF current flowed through paths P2-P5 in FIG. 10, it could cause an electrical shock or burn on the surgeon's arm 452 and/or the contact point on the patient's leg 454.

In order to reduce or prevent the possibility of such inadvertent RF current paths P2-P5 as shown in FIG. 10, components within the hub 465 of the probe 408 are provided with specific designs and parameters that are shown in FIGS. 11A-11C. Referring to FIG. 11A, the hub 465 is coupled to the elongated shaft 466 that extends to the working end 410 as shown in FIG. 10. The shaft 466 includes an outer sleeve 470 and concentric inner sleeve 475 that is adapted to rotate within the outer sleeve 470.

As can be seen in FIG. 11A, the outer sleeve 470 is fixed to hub 465 and the outer sleeve includes an outer insulator layer 476 that extends to a distal end 477 thereof shown in the bubble of FIG. 10. The inner sleeve 475 also includes an outer insulator layer 478 to thereby electrically insulate the inner sleeve 475 from the outer sleeve 470. The hub 465 can comprise a molded plastic body 480 that is adapted for detachable coupling to the receiving channel 482 in the handpiece 405 shown in phantom view in FIG. 11A As can be understood from FIG. 11A, the handpiece 405 and a receiving channel 482 carry a return electrical contact 485A and an active electrical contacts 485B that carry RF current from the RF source 425 (FIG. 10) to the probe 408 and the electrode arrangement in the working end 410. More in particular, the return electrical contact 485A in the hub 465 comprises an electrode ring that extends 360° around the receiving channel 482 of handpiece 405 and is adapted to interface with the corresponding return electrical contacts 488A, 488A' that are carried on opposing sides of the hub 465. Similarly, the active electrical contact 485B is another 360° ring electrode in the receiving channel 482 which is adapted to engage the active hub electrical contacts 488B. 488B' which are carried in opposing sides of the hub 465.

From viewing FIG. 11A, it can be further understood that outer sleeve 470 and inner sleeve 475 are formed of the electrically conductive material and are adapted to carry RF current to the active and return electrodes, 415 and 420, in the working end 410 (see FIG. 10). Thus, referring again to FIG. 11A, the return electrical contact 485A in handpiece 405 is electrically connected to the outer sleeve 470 and the active electrical contact 485B is electrically connected to the inner sleeve 475. More in particular, the return electrical contact 488A in the hub 465 is proximal to the active electrical contact 488B therein for reasons explained below. The electrical return hub contacts 488A, 488A' comprise spring-loaded elements 490, 490' that contact a thin-wall conductive cylindrical core 492 that is molded into the interior of the hub body 480. The core member 492 extends distally in the hub 465 to contact a metal block 495 that is adapted to connect to outer sleeve 470 as shown in FIG. 11A. Thus, an electrical current path is provided between the return electrical contacts 488A, 488A' and the outer sleeve 470 through the interior of the hub 465.

The active electrical contacts 488B, 488B' in the hub 465 again include spring ball elements 494, 494' that are adapted to engage the electrical contact 485B in the handpiece 405. Further, the electrical contacts 488B, 488B' are configured to carry RF current and engage a rotating collar 496 which is fixed to the proximal and 498 of inner sleeve 475. As can be understood from FIGS. 1, 2A and 2B, the rotational inner sleeve 475 and collar 496 of FIG. 11A are fixed to the coupling shaft 502 which detachably engages with motor shaft 505 when the probe hub 465 is attached to the handpiece 405. Still referring to FIG. 1A, a fluid flow path extends through the lumen 510 of inner sleeve 475 and the cooperating bore 512 in coupling shaft 502 that extends to exit port 515 in the coupling shaft 512. In FIG. 11A, it can be seen how fluid exits the port 515 in the coupling shaft 512 and then is confined in annular chamber 520 in the hub 465 and further communicates with outflow channel 522 in the handpiece 405.

Still referring to FIG. 11A, it can be seen that the inner sleeve 475 and coupling shaft 502 rotate within polymer retaining collar 524 that is locked into the hub body 480 by a molded locking ring 525 that is configured for a snap-fit into the hub body 480 to hold the retaining collar 524 in place. It can be seen that the distal and 528 of the retaining collar 524 abuts the flange portion 540 of the rotating collar 496 to prevent axial movement of the inner sleeve 475. A 360° seal 545 is provided around the rotating collar 496 to limit fluid flows from chamber 548 which can fill with saline 460 during a procedure and is exposed to our current flow from the electrical contacts 488B and 488B'. It has been found that during a surgical procedure, the saline outflows through the probe will migrate through all the gaps and interfaces between components in the interior of the hub 465. Thus, the rotational interface R between the retaining collar 496 and the rotating coupling shaft 502 will fill with saline. The rotational interface R will be exposed to saline or other fluid migration from chamber 520. In some variations, the rotational interface R can be filled with a viscous fluid or grease to prevent saline migration into the interface.

In FIG. 11A, it also can be seen that there is non-rotating interface NR between the outer surface of the retaining collar 524 and the proximal hub body 480' which is also susceptible to saline or other fluid migration. The interface NR again is exposed to saline 460 that can migrate from chamber 520 into the interface.

Still referring to FIG. 11A, O-rings 552 in 554 are provided in the exterior of the hub 465 to prevent saline or other fluid migration between the opposing polarity handpiece electrical contacts 485A and 485B in the corresponding hub electrical contacts.

Now having described the electrical components and features of handpiece 405 and probe hub 465, it can be explained how the design of the hub components addresses the issue of inadvertent and unwanted RF current paths (P2-P5) described above and illustrated in FIG. 10.

Referring again to FIG. 11A, a potential known RF current path KP1 is shown that extends from the most proximal portion of an exposed inner sleeve 475 (which is carrying RF current to active electrode 415 at working end 410) and the return electrical contact 485A in handpiece 405. It should be appreciated that the gap G between the outer surface of the hub body 480 and the receiving channel 482 of the handpiece 405 is quite large in terms of conducting RF current since saline will easily migrate into the gap G. Thus, it can be understood why is important to design the hub 465 so that the return electrical contact 485A is more proximal than the active electrical contact 485B. The return electrical contact 485A is intentionally exposed to saline flows in interior chamber 520 to thus provide a known, controllable RF current path through the saline outflow. Further, the O-ring seal 552 prevents saline or other fluid migration from interior chamber 520 to the active electrical contact 485B. Thus, it can be understood that the known RF current path KP1 is intentionally provided and can have a known lower impedance than the more circuitous RF current paths P2-P5 in FIG. 10. With this design, there should never be a situation in which RF potential will favor coupling through the surgeon's arm 452 and thereafter the patient's leg 454 as shown in FIG. 10. Rather, the RF current will flow through the known to have KP1 of FIG. 11A.

In FIG. 11A, the rotating coupling shaft 502 has an elongate sleeve portion 555 that extends distally in the bore 558 of the inner sleeve 475. It should be appreciated that the sleeve portion 555 which is an electrical insulator can extend any distance in the bore 510 of the inner sleeve 475 and can extend distally to the working end 410 the probe. Such an electrically insulating lining of the inner sleeve 475 can comprise a molded portion of the rotating coupling shaft 502 or any other separate component or insulating coating that lines the inner sleeve 475. The length of the current path KP1 then can be controlled to provide a selected impedance which is less than the circuitous RF current paths P2-P5 in FIG. 10. The current path KP1 is also designed or dimensioned to have a sufficiently high impedance to ensure that current path P1 (FIG. 10) is always the primary RF current path between the active and return electrodes 415, 420 (FIG. 10) for igniting plasma when intended.

Now turning to FIG. 11B, somewhat related issues arise concerning other predictable RF current paths within the interior of the hub 465. As described previously, the rotational interface R between the rotating coupling shaft 502 and the retaining collar 524 will fill with saline and carry RF current therein between active and return electrode components within the hub. This known current path is indicated at KP2 in FIG. 11B, and if allowed to be significant, could cause heating of the trapped saline and thereafter unwanted heating of the hub 465. Therefore, the dimensions of the space in the rotational interface Rare designed to be as small as possible, for example less than 0.010", which ensures that the path KP2 has a very high impedance and thus only limited RF current can follow this path.

FIG. 11 C illustrates another known current path indicated at KP3 which again could cause heating in the saline and unwanted heating of the hub 465. Current path KP3 is in the non-rotating interface NR between the retaining collar 524 and the proximal hub body portion 480'. The same issues arise as described previously, and therefore the dimensions across the non-rotating interface NR are designed to be as small as possible, for example less than 0.010", which ensures that the path KP3 has a very high impedance therein to limit RF current flow therethrough.

Figure 12:
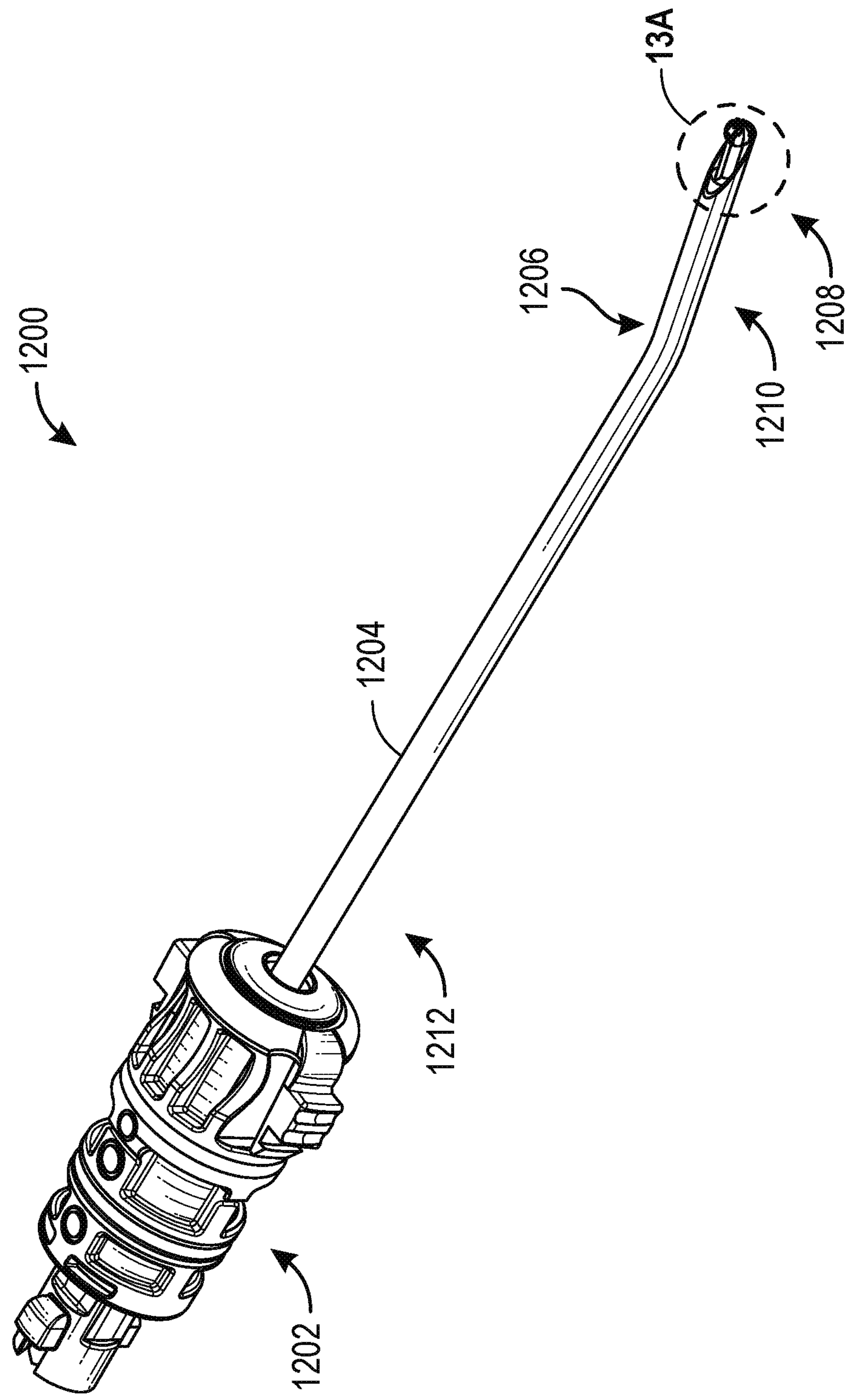
FIG. 12 shows an arthroscopic cutting system in accordance with at least one example disclosed herein.

FIG. 12 shows an arthroscopic cutting system 1200 in accordance with at least one example disclosed herein. Arthroscopic cutting system 1200 can include a hub 1202, an outer tube 1204, an inner tube 1302, and a wire tube 1304 (see FIGS. 13A, 13B, and 13C). As shown, outer tube 1204 can include a bend 1206. Bend 1206 can allow for a tip end 1208 to be inserted into various spaces during surgeries. While FIG. 12 shows a single bend, system 1200 can include a plurality of bends.

Bend 1206 can be a fixed angle. For example, bend 1206 can have a fixed angle of about 15°. Other fixed angles, such as 10°, 12.5°, 17.5°, 20°, etc. are also contemplated. System 1200 can be one of multiple systems and each of the systems may have a bend with a fixed angle that differs from other systems within the set of systems. While FIG. 12A shows bend 1206 located proximate a distal end 1210 of outer tube 1204, bend 1206 can be located in a central portion of outer tube 1204 and/or a proximal end 1212 of outer tube 1204.

The angle for bend 1206 can also be flexible. For example, outer tube 1204 can be constructed of a material malleable by a surgeon and the surgeon can bend or otherwise reshape a portion of outer tube 1204 to a desired angle. For example, outer tube 1204 may be manufactured from polymer or aluminum material that is bendable by the surgeon. During surgery, the surgeon can bend outer tube 1204 to a desired angle.

Figure 13A:
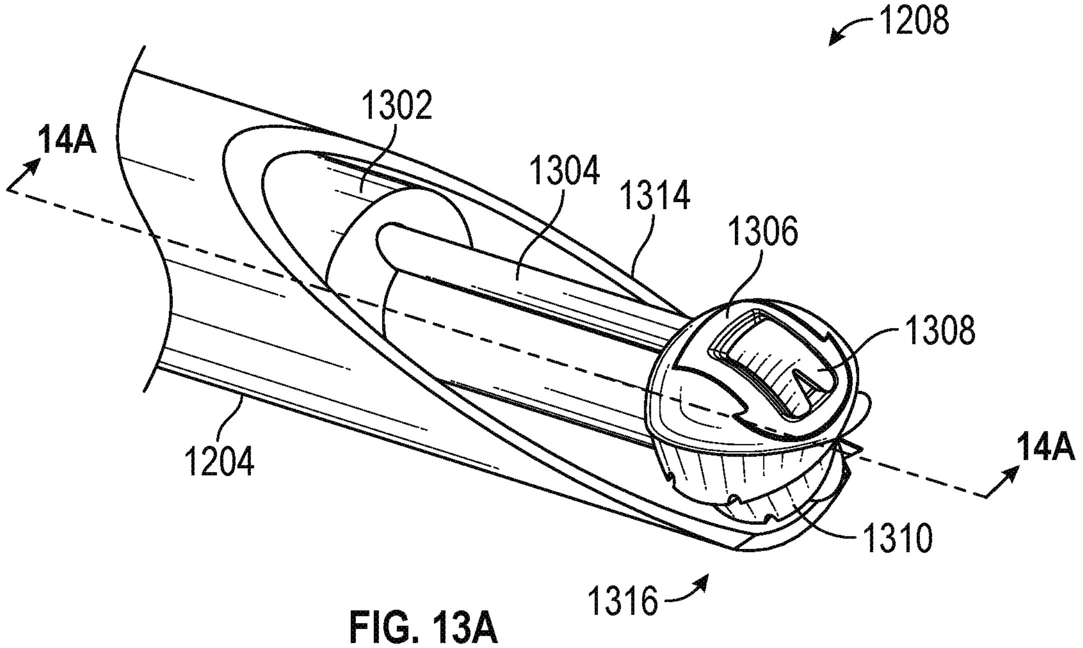
FIGS. 13A, 13B, 13C, and 13D show a tip end of an arthroscopic cutting system in accordance with at least one example disclosed herein.
Figure 13B:
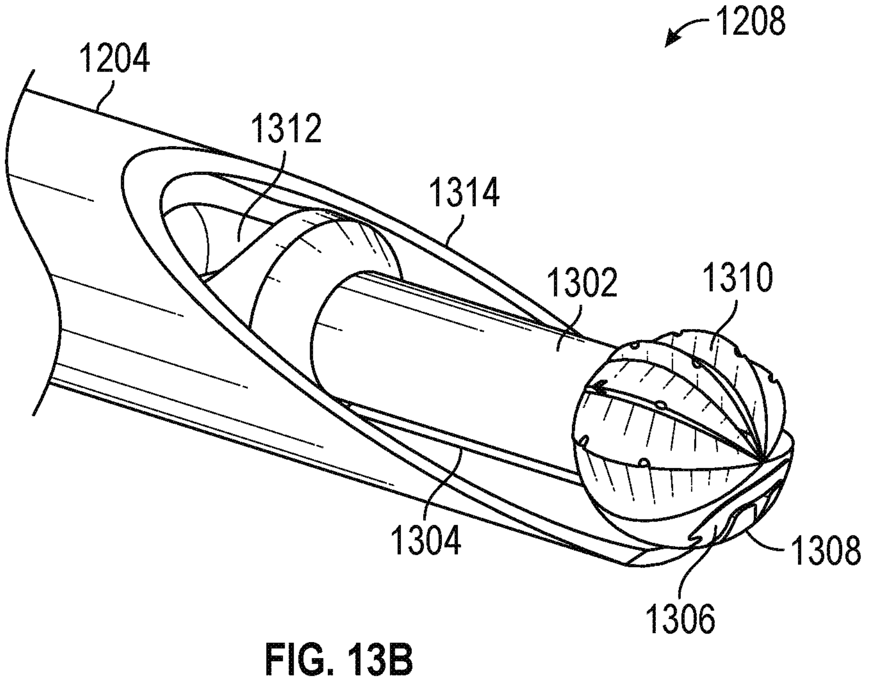
Figure 13C:
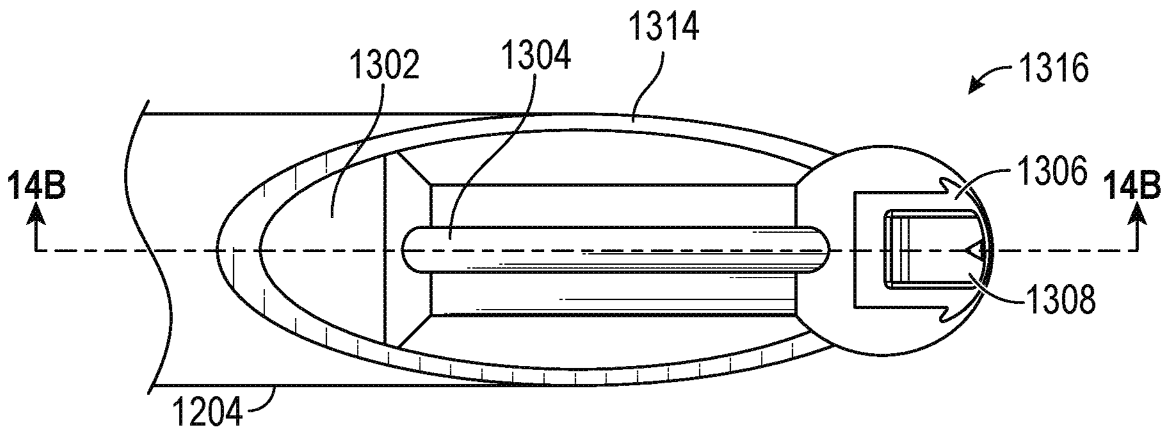
Figure 13D:
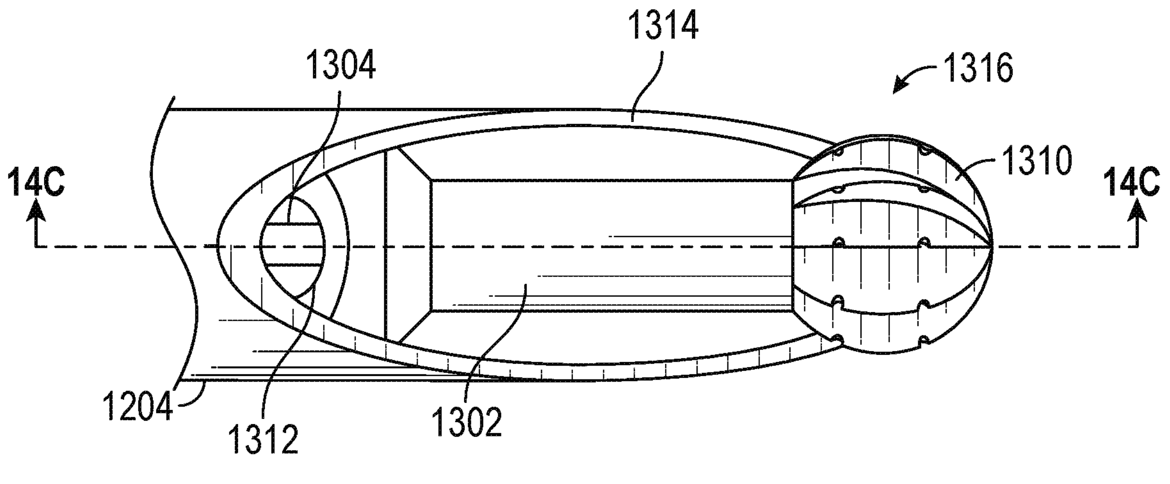

FIGS. 13A, 13B, 13C, and 13D show tip end 1208 in greater detail. Tip end 1208 may include a insulator 1306, an active electrode 1308, and a burr tool 1310. As shown in FIG. 13B, inner tube 1302 can define an opening 1312. During use, inner tube 1302 can rotate in a first direction (e.g., clockwise) and a second direction (e.g., counterclockwise) about a longitudinal axis of inner tube 1206. Outer tube 1204 and inner tube 1302 are coaxial, so while outer tube 1204 is fixed with respect to rotation, inner tube 1302 can also rotate in the first and second directions around a longitudinal axis of outer tube 1204. The longitudinal axis of outer tube 1204 and/or inner tube 1302 can be straight and/or curved to follow bend 1206. The longitudinal axis of outer tube 1204 and/or inner tube 1302 can extend from proximal end 1212 to distal end 1210.

Figure 14A:
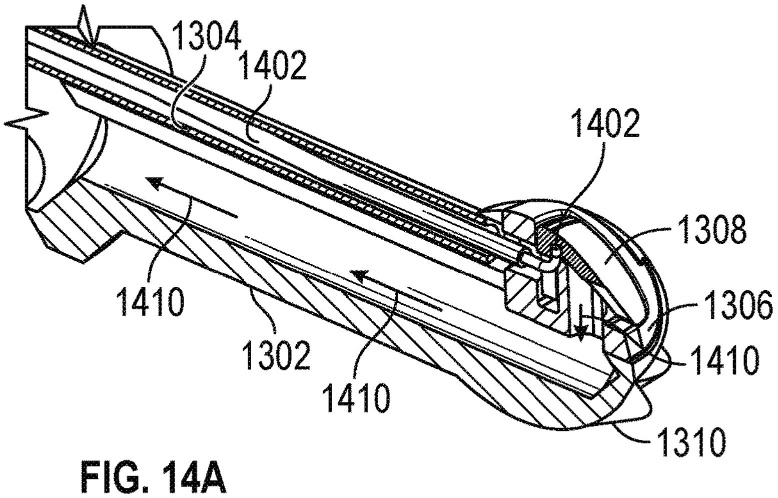
FIGS. 14A, 14B, and 14C show cross-sectional views of a tip end of an arthroscopic cutting system in accordance with at least one example disclosed herein.

As shown in FIG. 14A, a insulated wire 1402 can be located inside wire tube 1304. Wire 1402 can be a conductive material, such as copper, or alloy with a insulative non-conducting coating material, such as a polymer, so as to prevent RF energy from being conducted into burr tool 1310 and/or wire tube 1304. Wire 1402 can be connected to active electrode 1308. As disclosed herein, wire 1402 provides an electrically conductive path for electricity or other radio frequency or electromagnetic energy, referred to herein as RF energy to travel from hub 1202 to electrode 1308. During surgery, the RF energy can be used to cauterize or ablate tissue. Insulator 1306 can be a non-conducting material, such as a ceramic, so as to prevent RF energy from being conducted into burr tool 1310 and/or wire tube 1304.

Figure 14B:
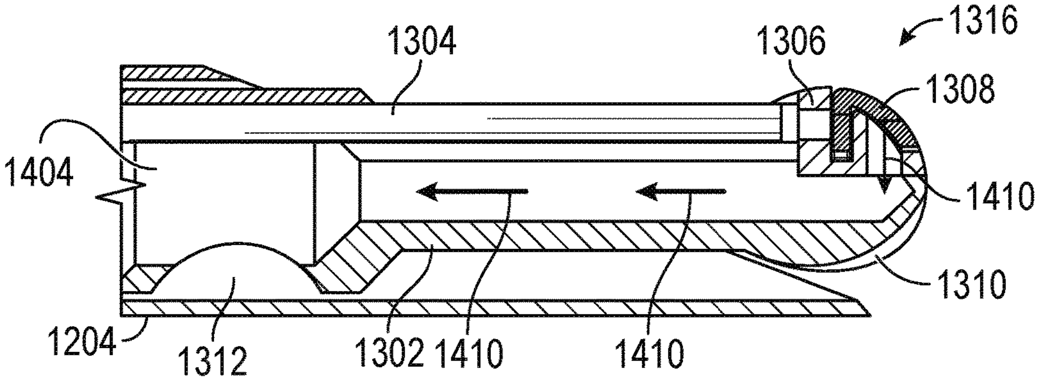
Figure 14C:
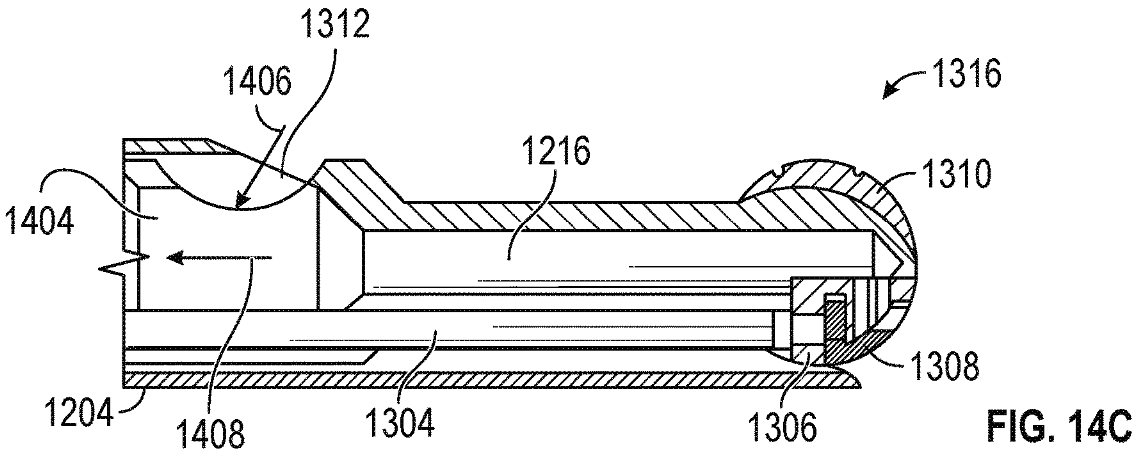

In addition to providing RF energy for cauterization and/or ablation, system 1200 also provides a channel for removal of tissue. As shown in FIGS. 13B and 14C, opening 1312 defined by inner tube 1302 provides a pathway for tissue to enter a cavity 1404 defined by inner tube 1302 as indicated by arrow 1406. Opening 1312 proximate distal end 1210, in conjunction with inner tube 1302, can define a fluid pathway extending from opening 1312 to proximal end 1212 during a burring operation, Once inside cavity 1404, the tissue can travel toward hub 1202, which can be connected to a vacuum source as disclosed herein, as indicated by arrow 1408.

As shown in FIGS. 13A and 13B, inner tube 1302 can be located at least partially inside outer tube 1204. For example, inner tube 1302 can extend from hub 1202 to a distal end of outer tube 1204. As further shown in FIGS. 13A and 13B, outer tube 1204 can have a relief 1314 that can partially encircle a portion of inner tube 1302. Relief 1314 can protect surrounding tissue during rotation of inner tube 1302.

As shown in FIG. 13A, wire tube 1304 can be located at least partially inside inner tube 1302. For example, wire tube 1304 can extend from hub 1202 to a distal end of inner tube 1302. Wire tube 1304 can extend into a head portion 1316 and allow wire 1402 to connect with electrode 1308. Head portion 1316 can define burr tool 1310 and a recess 1502 (see FIG. 15A) for receiving insulator 1306 and electrode 1308.

Figure 15A:
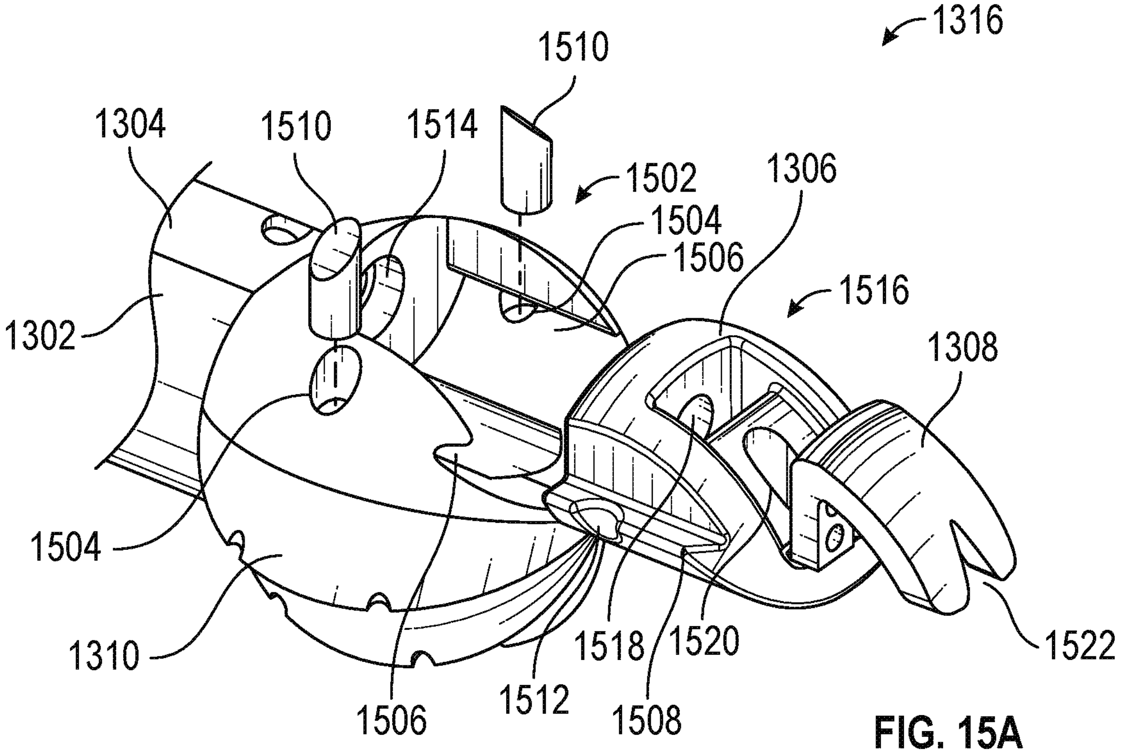
FIGS. 15A and 15B show ahead portion of an inner tube in accordance with at least one example disclosed herein.
Figure 15B:
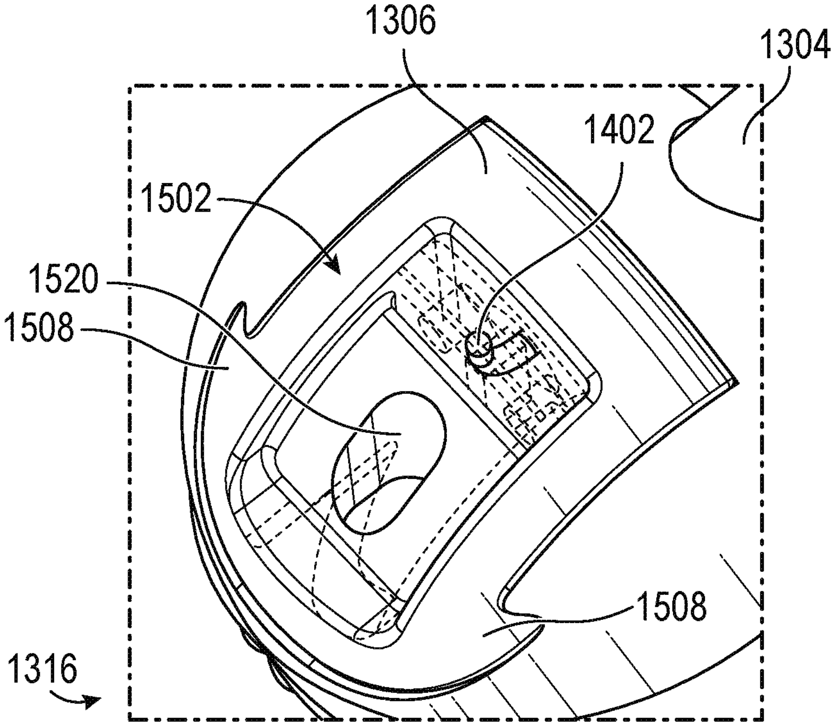

FIGS. 15A and 15B show head portion 1316 in accordance with at least one example disclosed herein. As shown in FIG. 15A, head portion 1316 can define recess 1502 and holes 1504. Head portion 1316 can further define grooves 1506, which are shaped complementary to projections 1508 defined by insulator 1306. During assembly, insulator 1306 can be slid into recess 1502 and secured by pins 1510. Upon sliding into holes 1504, pins 1510 may rest against complementary indentions 1512 defined by insulator 1512.

Head portion 1316 can define a hole 1514 that allows wire 1402 to pass from wire tube 1304 into head portion 1316 and a recess 1502 defined by insulator 1306. Insulator 1306 can also define a hole 1518 to allow wire 1402 to pass into recess 1502. Electrode 1308 can be connected to wire 1402 within recess 1502.

Insulator 1306 can define a hole 1520 that allows tissue and other fluids to flow from an exterior of system 1200 into inner tube 1302. Electrode 1308 can define a hole or notch 1522 to allow fluid and tissue to flow into inner tube 1302. Hole 1520 and notch 1522 can form a fluid pathway, in conjunction with inner tube 1302 and shown by arrows 1410, from distal end 1210 to hub 1202 during an ablation operation. For example, as shown in FIG. 14B, during use suction created within inner tube 1302 can cause tissue and fluids to flow through notch 1522 and hole 1520 into inner tube 1302. The fluids and tissue can then be evacuated from a patient via hub 1202 as disclosed herein.

Figure 16A:
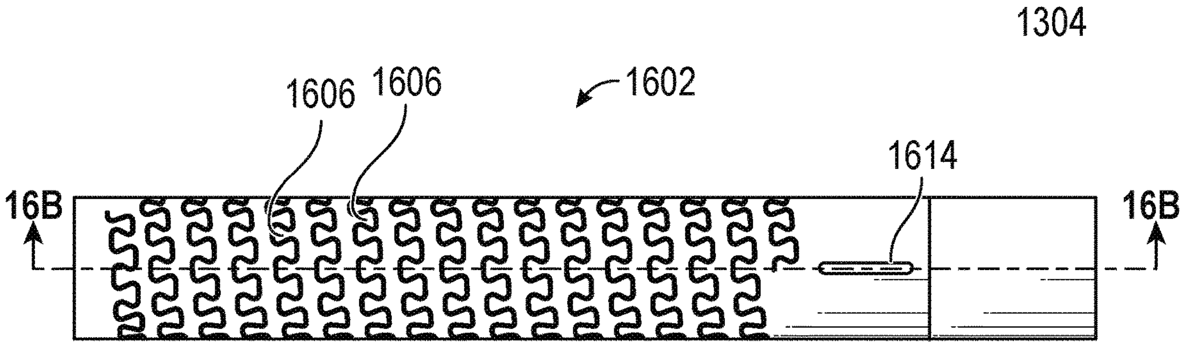
FIGS. 16A, 16B, and 16C show segmented portions of an inner tube and a wire tube in accordance with at least one example disclosed herein.
Figure 16B:
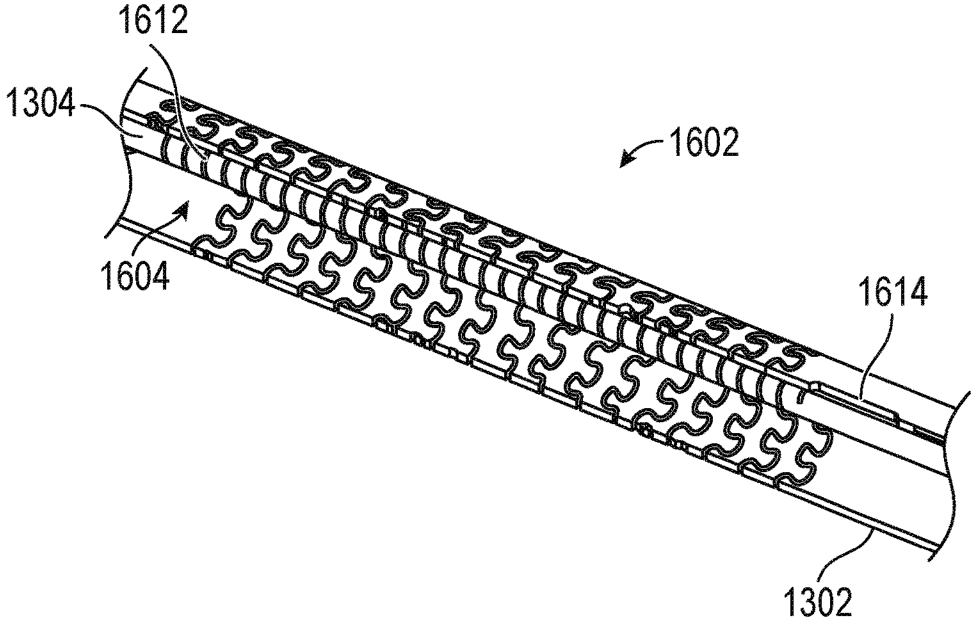
Figure 16C:
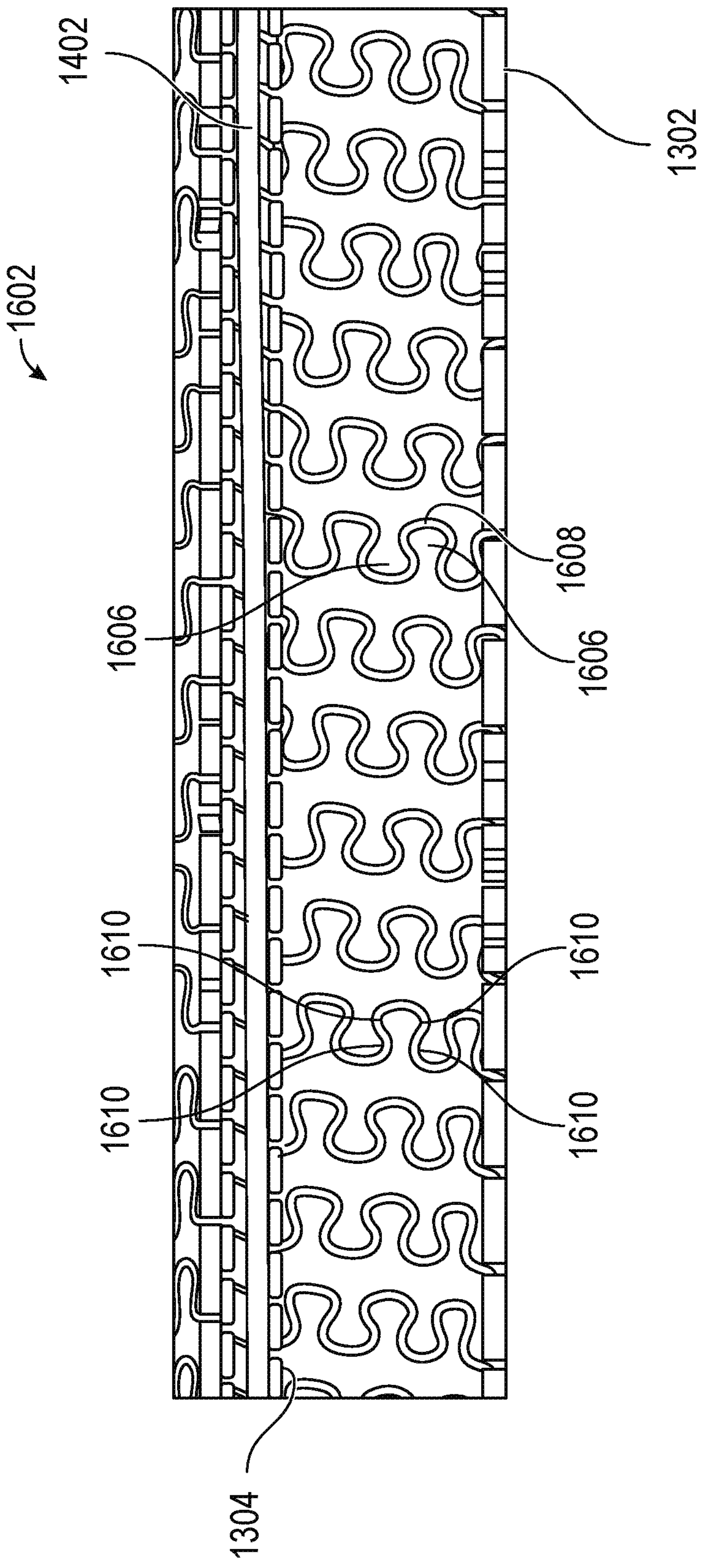

As disclosed herein, inner tube 1302 and wire tube 1304 can rotate about a longitudinal axis of outer tube 1204. As a result, inner tube 1302 and wire tube 1304 can flex proximate bend 1206. Inner tube 1302 and wire tube 1304 can each define a segmented portion 1602 and 1604, respectively, as shown in FIGS. 16A, 16B, and 16C. As disclosed herein, segmented portions 1602 and 1604 allow inner tube 1302 and wire tube 1304 to flex.

As disclosed herein, inner tube 1302 can be rotated and stopped in a selected position. For example, inner tube 1302 can be stopped so that opening 1312 is exposed to allow a surgeon to utilize tip end 1208 for suction to remove tissue and/or fluids without shaving and/or ablating tissue. Inner tube 1302 can be stopped so that electrode 1308 is exposed as shown in FIG. 13A to allow the surgeon to use tip end 1208 for ablation. To stop inner tube 1302 in a desired position a controller algorithm can be used to stop movement of inner tube 1302 as disclosed herein, such as motor drive 105 coupled to rotating drive coupling 150, and thus sensing the position of opening 1312 and/or inner tube 1302. The controller algorithm can used drive coupling 150 magnets 255*a* or 255*b* and/or Hall sensor 245 as disclosed herein to control the position of inner tube 1302 as well as the speed at which inner tube 1302 rotates as disclosed above.

Segmented portion 1602 also allows for the transmission of torque in both the first and second directions of rotation. Segmented portion 1602 can include a plurality of interlocking fingers 1606. Interlocking fingers 1606 can be spaced apart by a space 1608. Space 1608 can allow interlocking fingers 1606 to move relative to one another. Interlocking fingers 1606 can include lobes 1610. Lobes 1610 can provide column and tensile strength to inner tube 1302 so that inner tube 1302 can be inserted and removed from outer tube 1204.

Segmented portion 1604 of wire tube 1302 can have a spiral cut 1612. Spiral cut 1612 can allow wire tube 1304 to flex during rotation. As inner tube spins, wire tube 1304 can expand and contract via spiral cut 1612. For example, spiral cut 1612 can be a helical cut having a pitch that allows wire tube 1304 to expand and contract at segmented portion 1604. Inner tube 1302 can define one or more openings 1614, which can be located on both sides of segmented portion 1602. During manufacturing, wire tube 1304 can be connected to, such as by welding, to inner tube 1302 via openings 1614.

Figure 17:
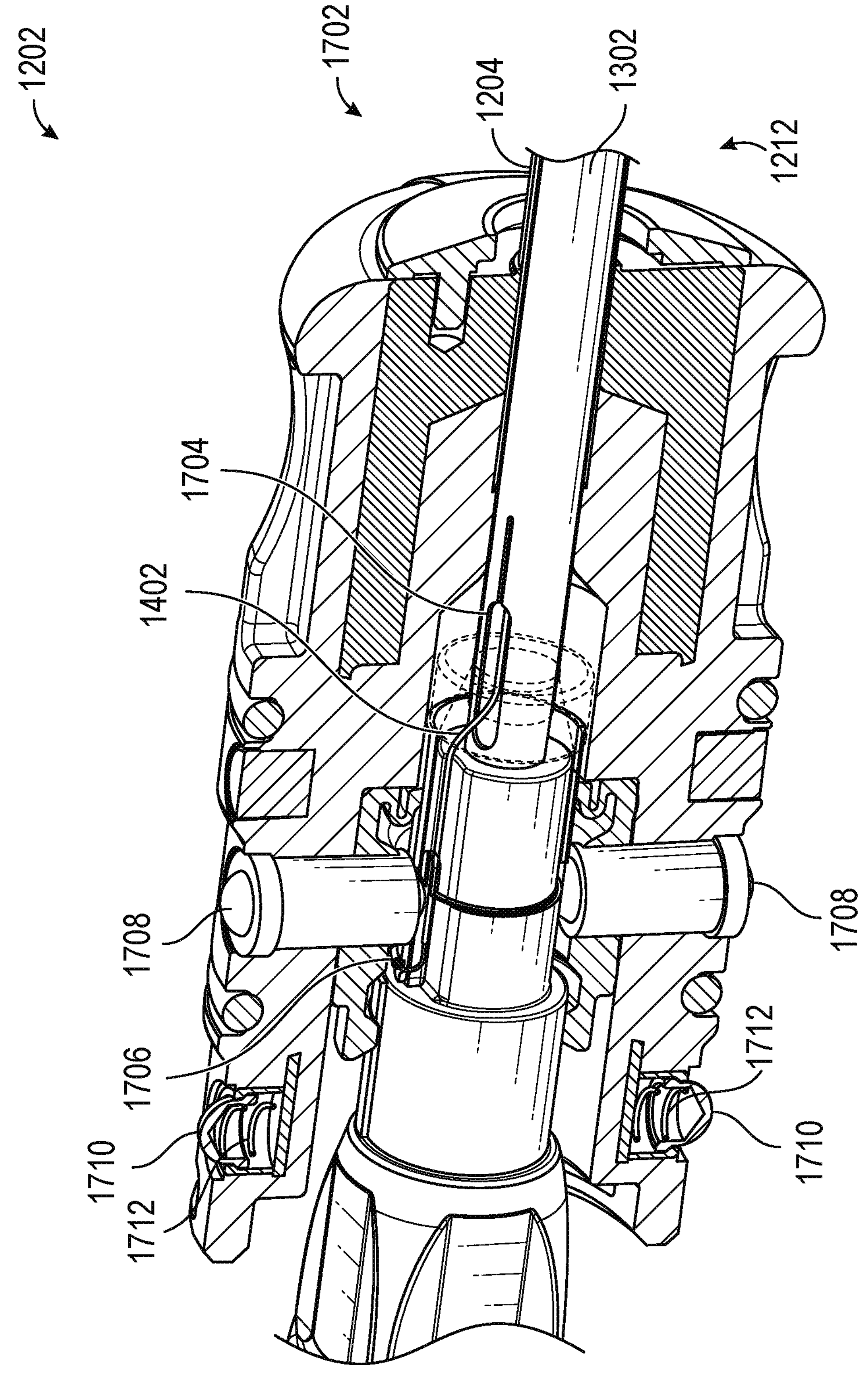
FIG. 17 shows a hub in accordance with at least one example disclosed herein.

FIG. 17 shows a cross-sectional view of hub 1202 in accordance with at least one example disclosed herein. As shown in FIG. 17, proximal end 1212 of outer tube 1204 and inner tube 1302 can be inserted into a distal end 1702 of hub 1202. Inner tube 1302 can define an opening 1704 that allows wire 1402 to exit inner tube 1302. During use, hub 1202 can also cause inner tube 1304 to rotate clockwise and counterclockwise as disclosed above.

Wire 1402 can connect to an electrode contact 1706. Electrode contact 1706 can connect to one or more active RF contacts 1708 as inner tube 1302 rotates. Active RF contacts 1708 can contact an active RF ring within a handpiece as disclosed above. Hub 1202 can also include one or more return RF contacts 1710. During use, RF energy can be transmitted from active RF contacts 1708 to electrode contact 1706. The RF energy can then travel via wire 1402 to electrode 1308. After ablation takes place, the RF energy can return to return RF contacts 1710 via outer tube 1204 and/or inner tube 1302. RF contacts 1710 can be in electrical communication with a return RF ring within the handpiece as disclosed above.

As shown in FIG. 17, hub 1202 can include one or more springs 1712 (not shown for active RF contacts 1708). Springs 1712 can press active RF contacts 1708 and return RF contacts 1710 into contact with an active RF and return RF rings within the handpiece. The springs can allow for continued electrical communication during rotation since springs 1712 can be electrically conductive and therefore carry RF energy between electrode contact 1706 and RF contacts 1708 and 1710.

Figure 18:
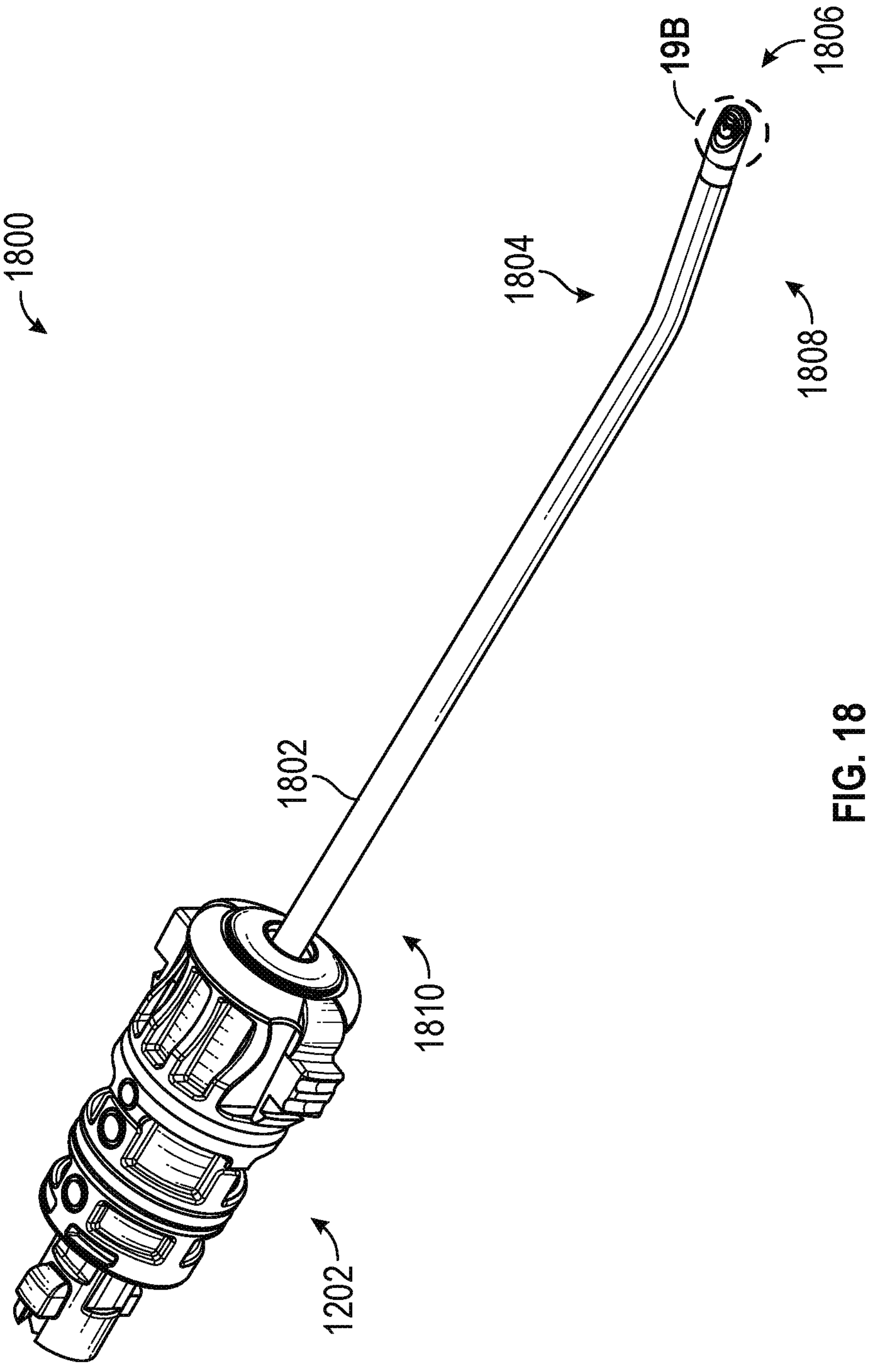
FIG. 18 shows an arthroscopic cutting system in accordance with at least one example disclosed herein.

FIG. 18 shows an arthroscopic cutting system 1800 in accordance with at least one example disclosed herein. Arthroscopic cutting system 1800 can include hub 1202, an outer tube 1802, inner tube 1902, and a wire tube as disclosed above, but not shown in FIGS. 18, 19A, and 19B. As shown, outer tube 1802 can include a bend 1804. Bend

1804 can allow for a tip end 1806, sometimes referred to as a probe, to be inserted into various spaces during surgeries. While FIG. 18 shows a single bend, system 1800 can include a plurality of bends.

Bend 1804 can have a fixed angled or an adjustable angle as disclosed above. System 1800 can be one of multiple systems and each of the systems may have a bend with a fixed angle that differs from other systems within the set of systems and/or be adjustable angles. While FIG. 18 shows bend 1804 located proximate a distal end 1808 of outer tube 1802, bend 1804 can be located in a central portion of outer tube 1802 and/or a proximal end 1810 of outer tube 1802.

Figure 19A:
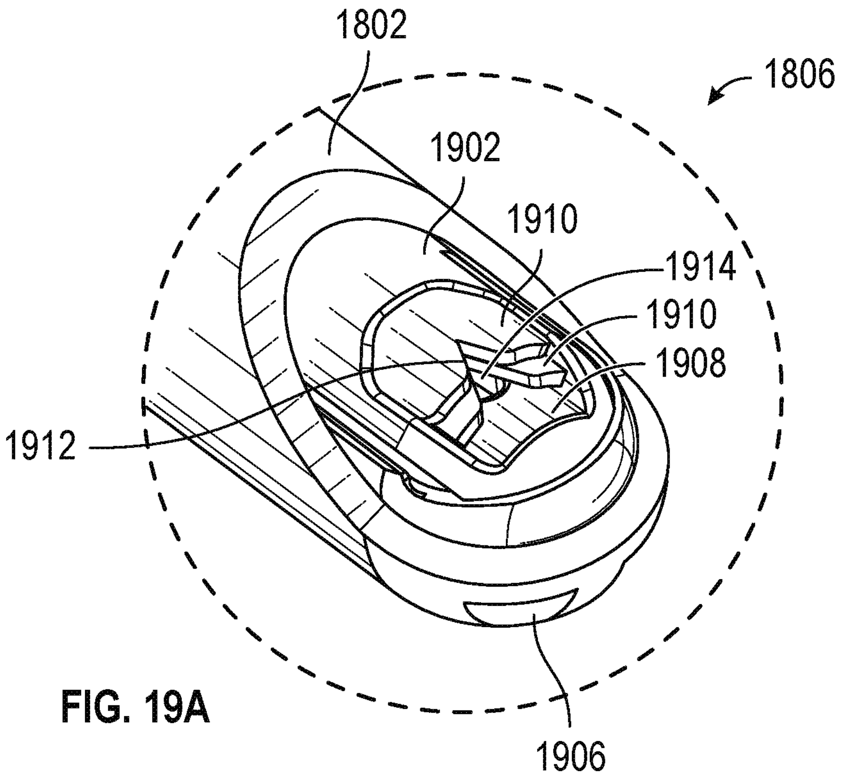
FIGS. 19A and 19B show a tip end of an arthroscopic cutting system in accordance with at least one example disclosed herein.
Figure 19B:
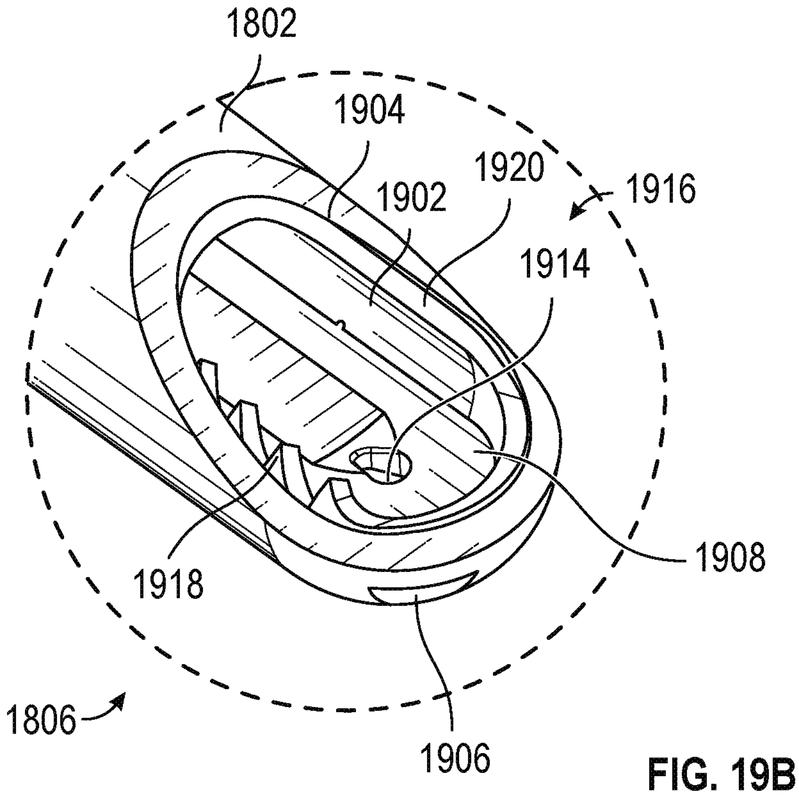

FIGS. 19A and 19B show tip end 1806 of arthroscopic cutting system 1800 in accordance with at least one example disclosed herein. As shown in FIGS. 19A and 19B, outer tube 1802 can define a first opening 1904 and a second opening 1906. System 1800 can also include an insulator 1908 and one or more active electrodes 1910. Active electrodes 1910 can each define a notch 1912. Insulator 1908 can define a hole 1914. During an ablation operation RF energy can travel via a wire (not shown) from hub 1202 to active electrode 1910 as disclosed above. Notches 1912 and hole 1914 can allow fluids and/or tissue to be drawn through inner tube 1902 via suction created by a handpiece as disclosed herein. The suction can also draw fluids and/or tissue through opening 1906.

Inner tube 1902 can define a shaver tool 1916. Shaver tool 1916 can include a serrated edge 1918 and a sharpened edge 1920. During rotation in a first direction, such as clockwise, serrated edge 1918 can engaged bone and/or tissue. During rotation in a second direction, such as counterclockwise, sharpened edge 1920 can engage bone and/or tissue.

As disclosed herein, inner tube 1902 can be rotated and stopped in a selected position. For example, inner tube 1902 can be stopped so that opening 1904 is exposed to allow a surgeon to utilize tip end 1806 for suction to remove tissue and/or fluids without shaving and/or ablating tissue. Inner tube 1902 can be stopped so that electrode 1910 is exposed as shown in FIG. 19A to allow the surgeon to use tip end 1806 for ablation. To stop inner tube 1902 in a desired position a controller algorithm can be used to stop movement of inner tube 1902 as disclosed herein, such as motor drive 105 coupled to rotating drive coupling 150, and thus sensing the position of opening 1904 and/or inner tube 1902. The controller algorithm can used drive coupling 150 magnets 255_a_ or 255_b_ and/or Hall sensor 245 as disclosed herein to control the position of inner tube 1902 as well as the speed at which inner tube 1902 rotates as disclosed above.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A device for treating tissue, comprising:

an outer tube having an axis that extends from a proximal end to a distal end of the outer tube, the outer tube forming a bend located proximate the distal end of the outer tube;

an inner tube located at least partially inside the outer tube and extending from the proximal end of the outer tube to the distal end of the outer tube, the inner tube defining a first segmented portion located at the bend of the outer tube;

a wire tube located at least partially inside the inner tube and extending from the proximal end of the outer tube to the distal end of the outer tube, the wire tube defining a second segmented portion located at the bend of the outer tube and the first segmented portion;

an electrode connected to the inner tube at a distal end of the inner tube; and a wire located at least partially inside the wire tube and connected to the electrode, the wire extending from the electrode to the proximal end of the outer tube, wherein the first segmented portion and the second segmented portion are each configured to allow the inner tube, the wire tube, and the wire, to respectively flex proximate the bend upon rotation of the inner tube, the wire tube, and the wire about the axis of the outer tube.

2. The device of claim 1, wherein the first segmented portion includes a plurality of interlocking fingers.

3. The device of claim 1, wherein the second segmented portion is defined by a spiral patterned cut formed in the wire tube.

4. The device of claim 1, wherein the wire tube is connected to the inner tube proximate a distal end and a proximal end of the first segmented portion.

5. The device of claim 1, wherein the inner tube defines:

a first opening proximate the distal end of the outer tube and communicating with a first fluid pathway extending from the first opening to the proximal end of the outer tube, and a second opening located in between the first opening and the proximal end of the outer tube and communicating with the first fluid pathway.

6. The device of claim 1, wherein the electrode is recessed into a ceramic insulator attached to a distal end of the inner tube.

7. The device of claim 1, further comprising a burr tool located proximate the electrode.

8. The device of claim 1, further comprising a shaver tool located proximate the electrode.

9. The device of claim 1, further comprising a hub attached to the proximal end of the outer tube, the hub detachably connectable to a handpiece.

10. The device of claim 9, wherein the hub comprises an active radiofrequency contact in electrical communication with the wire.

11. A device for treating tissue, the device comprising:

an outer tube having an axis that extends from a proximal end to a distal end of the outer tube, the outer tube forming a bend located proximate the distal end of the outer tube;

an inner tube located at least partially inside the outer tube and extending from the proximal end of the outer tube to the distal end of the outer tube, the inner tube defining a first segmented portion located at the bend of the outer tube;

a wire tube located at least partially inside the inner tube and extending from the proximal end of the outer tube to the distal end of the outer tube, the wire tube defining a second segmented portion located at the bend of the outer tube and the first segmented portion;

a tip assembly located at a distal end of the inner tube, the tip assembly including a cutting surface, a ceramic insulator located in a first recess in the tip assembly, and an electrode located in a second recess in the ceramic insulator; and a wire located at least partially inside the wire tube and connected to the electrode, the wire extending from the electrode to the proximal end of the outer tube, wherein the first segmented portion and the second segmented portion are each configured to allow the inner tube, the wire tube, and the wire, to respectively flex proximate the bend upon rotation of the inner tube, the wire tube, and the wire about the axis of the outer tube.

12. The device of claim 11, wherein the first segmented portion includes a plurality of interlocking fingers.

13. The device of claim 11, wherein the second segmented portion is defined by a spiral patterned cut formed in the wire tube.

14. The device of claim 11, wherein the wire tube is connected to the inner tube proximate a distal end and a proximal end of the first segmented portion.

15. The device of claim 11, wherein the tip assembly includes a burr tool located proximate the electrode.

16. The device of claim 15, wherein the ceramic insulator is slidable into the first recess in the tip assembly in an axial direction, and wherein the electrode is slidable into the second recess in the ceramic insulator in a section direction transverse to the axial direction.

17. The device of claim 11, wherein the tip assembly includes a shaver tool located proximate the electrode.

18. The device of claim 11, wherein the inner tube defines:

a first opening proximate the distal end of the outer tube and communicating with a first fluid pathway extending from the first opening to the proximal end of the outer tube, and a second opening located in between the first opening and the proximal end of the outer tube and communicating with the first fluid pathway.

19. The device of claim 11, further comprising a hub attached to the proximal end of the outer tube, the hub detachably connectable to a handpiece.

20. The device of claim 19, wherein the hub comprises an active radiofrequency contact in electrical communication with the wire.

* * * * *